(12) United States Patent
James et al.

(10) Patent No.: US 10,167,387 B2
(45) Date of Patent: Jan. 1, 2019

(54) SYNTHETIC POLYMERIC MATERIALS AND DEVICES THEREOF

(71) Applicant: Colorado State University Research Foundation, Fort Collins, CO (US)

(72) Inventors: Susan P. James, Bellvue, CO (US); Travis S. Bailey, Fort Collins, CO (US); Ketul C. Popat, Fort Collins, CO (US); David A. Prawel, Loveland, CO (US); Jackson T. Lewis, Fort Collins, CO (US); Richard L. Koch, Milford, KS (US)

(73) Assignee: Colorado State University Research Foundation, Fort Collins, CO (US)

( * ) Notice: Subject to any disclaimer, the term of this patent is extended or adjusted under 35 U.S.C. 154(b) by 54 days.

(21) Appl. No.: 14/917,795

(22) PCT Filed: Sep. 10, 2014

(86) PCT No.: PCT/US2014/054898
§ 371 (c)(1),
(2) Date: Mar. 9, 2016

(87) PCT Pub. No.: WO2015/038577
PCT Pub. Date: Mar. 19, 2015

(65) Prior Publication Data
US 2016/0222203 A1    Aug. 4, 2016

Related U.S. Application Data

(60) Provisional application No. 61/876,148, filed on Sep. 10, 2013.

(51) Int. Cl.
*A61F 2/16*      (2006.01)
*A61L 27/44*     (2006.01)
(Continued)

(52) U.S. Cl.
CPC ............. *C08L 43/04* (2013.01); *A61F 2/16* (2013.01); *A61L 27/44* (2013.01); *A61L 27/48* (2013.01); *C08G 77/388* (2013.01); *G02B 1/043* (2013.01); *G02C 7/049* (2013.01); *A61F 2002/1681* (2013.01)

(58) Field of Classification Search
None
See application file for complete search history.

(56) References Cited

U.S. PATENT DOCUMENTS 4,500,676 A * 2/1985 Balazs .............. A61L 27/26
424/423
4,633,003 A    12/1986 Falcetta et al.
(Continued)

FOREIGN PATENT DOCUMENTS

EP      0220919 A2    5/1987
JP      57-099611 A    6/1982
(Continued)

OTHER PUBLICATIONS

Schante et al. Chemical modifications of hyaluronic acid for the synthesis of derivatives for a broad range of biomedical applications, Carbohydrate Polymers 85, 2011, 469-489 (Year: 2011).*
(Continued)

*Primary Examiner* — Peter A Salamon
(74) *Attorney, Agent, or Firm* — Polsinelli PC

(57) ABSTRACT

Provided herein is a polymeric material comprising a polymer host; and a guest molecule comprising a glycosaminoglycan; wherein the guest molecule is disposed within the polymer host, and wherein the guest molecule is covalently bonded to at least one other guest molecule. In some embodiments, the polymer host comprises a silicone-based polymer. In other embodiments, the glycosaminoglycan is chosen from hyaluronic acid and derivatives thereof.

9 Claims, 18 Drawing Sheets

(51) Int. Cl.
*A61L 27/48* (2006.01)
*C08G 77/388* (2006.01)
*C08G 77/14* (2006.01)
*C08L 43/04* (2006.01)
*G02B 1/04* (2006.01)
*G02C 7/04* (2006.01)

(56) References Cited

U.S. PATENT DOCUMENTS

| | | | |
|---|---|---|---|
| 4,640,941 | A | 2/1987 | Park et al. |
| 4,737,558 | A | 4/1988 | Falcetta et al. |
| 5,962,548 | A | 10/1999 | Vanderlaan et al. |
| 6,861,123 | B2 | 3/2005 | Turner et al. |
| 7,521,488 | B2 | 4/2009 | Steffen et al. |
| 7,585,900 | B2 | 9/2009 | Cordova et al. |
| 7,825,170 | B2 | 11/2010 | Steffen et al. |
| 8,318,144 | B2 | 11/2012 | Ketelson et al. |
| 2003/0027967 | A1 | 2/2003 | Hori et al. |
| 2006/0293277 | A1* | 12/2006 | Leshchiner ............ A61K 8/735 514/54 |
| 2007/0292496 | A1 | 12/2007 | Herrero Vanrell et al. |
| 2012/0172486 | A1 | 7/2012 | Zhu et al. |
| 2013/0129844 | A1 | 5/2013 | Claret et al. |
| 2013/0209755 | A1 | 8/2013 | Hustad et al. |
| 2013/0274332 | A1 | 10/2013 | Furumiya et al. |
| 2015/0036100 | A1 | 2/2015 | Gorne et al. |

FOREIGN PATENT DOCUMENTS

| | | |
|---|---|---|
| WO | WO 91/07687 | 5/1991 |
| WO | WO 01/05578 A1 | 1/2001 |
| WO | WO 2010/025708 A1 | 3/2010 |
| WO | WO 2012/027834 A1 | 3/2012 |

OTHER PUBLICATIONS

Alauzun JG et al. Biocompatible, hyaluronic acid modified silicone elastomers. Biomaterials vol. 31, No. 13, May 1, 2010, pp. 3471-3478.
European Search Report, EP14843476.4, dated Mar. 2, 2017.
Rah MJ. A review of hyaluronan and its ophthalmic applications. *Optometry* 2011; 82:38-43.
Weeks A et al. Photocrosslinkable hyaluronic acid as an internal wetting agent in model conventional and silicone hydrogel contact lenses. Journal of Biomedical Materials Research Part A, vol. 100A, No. 8, Aug. 5, 2012, pp. 1972-1982.
De Boulle K et al. A Review of the Metabolism of 1,4-Butanediol Diglycidyl Ether-Crosslinked Hyaluronic Acid Dermal Fillers. *Dermatol Surg.* 2013;39:1758-1766.
Guo C, Bailey TS. Highly distensible nanostructured elastic hydrogels from AB diblock and ABA triblock copolymer melt blends. *Soft Matter.* 2010;6:4807-4818.
Ibrahim S, Kathapalli CR, Kang QK, Ramamurthi A. Characterization of glycidyl methacrylate—Crosslinked hyaluronan hydrogel scaffolds incorporating elastogenic hyaluronan oligomers. *Acta Biomaterialia.* 2011;7:653-665.
International Search Report and Written Opinion, PCT/US2014/054898, dated Dec. 4, 2014.
Leach JB, Bivens KA, Collins CN, Schmidt, CE. Development of photocrosslinkable hyaluronic acid-polyethylene glycol-peptide composite hydrogels for soft tissue engineering. *J Biomed Mater Res.* 2004;70A:74-82.
Scalfani VF, Bailey TS. Access to Nanostructured Hydrogel Networks through Photocured Body-Centered Cubic Block Copolymer Melts. *Macromolecules.* 2011;44:6557-6567.
Scalfani VF, Bailey TS. Thermally Stable Photocuring Chemistry for Selective Morphological Trapping in Block Copolymer Melt Systems. *Chem Mater.* 2010;22:5992-6000.
Skaalure SC, Dimson SO, Pennington AM, Bryant SJ. Semi-interpenetrating networks of hyaluronic acid in degradable PEG hydrogels for cartilage tissue engineering. *Acta Biomaterialia.* 2014;10:3409-3420.
Sun S, Schmidt CE. Photopatterned collagen-hyaluronic acid interpenetrating polymer network hydrogels. *Acta Biomaterialia.* 2009;5:2385-2397.
Van Beek M, Jones L, Sheardown H. Hyaluronic acid containing hydrogels for the reduction of protein adsorption. *J Biomaterials.* 2008;29:780-789.
Zawko SA, Sun S, Truong Q, Schmidt CE. Photopatterned anisotropic swelling of dual-crosslinked hyaluronic acid hydrogels. *Acta Biomaterialia.* 2009;5:14-22.

* cited by examiner $t_{rinse} = 0$ $t_{rinse} = 36$ hours $t_{rinse} = 60$ hours $t_{rinse}= 0$ $t_{rinse}= 60$ hours

SYNTHETIC POLYMERIC MATERIALS AND DEVICES THEREOF

CROSS-REFERENCE TO RELATED APPLICATIONS

This application is a National Stage application under 35 USC 371 of PCT/US2014/054898, filed Sep. 10, 2014, and published as WO 2015/038577 on Mar. 19, 2015, which claims the benefit of U.S. Provisional Application Ser. No. 61/876,148, filed Sep. 10, 2013, the entire contents of which are incorporated herein by reference in their entireties.

TECHNICAL FIELD

Aspects of the present disclosure relate to biocompatible materials, medical apparatuses and methods. More specifically, the present disclosure relates to polymer compositions, and to ocular or ophthalmic apparatuses.

BACKGROUND

Dry eye, ocular surface disease, and deficient tear syndrome each describes signs of clinical damage to the intrapalpebral ocular surface or symptoms of such disruption from a variety of causes. Included among dry eye-related ocular surface disorders is contact lens-related evaporative tear disruption. Contact lens wear can induce dry eye symptoms in patients who have a pre-existing, asymptomatic, marginally dry eye condition. Contact lens materials use greater surface wetting than the corneal epithelium. Wearing contact lenses thins the preocular tear film and interferes with the spreading of mucin onto the cornea. Thus, new contact lens materials are needed that are more hydrophilic.

In other cases, toxic anterior segment syndrome (TASS) is an acute severe intraocular inflammation accompanied by diffuse corneal edema within 1-2 days of anterior segment surgery most commonly associated with cataract surgery. TASS is a form of sterile, noninfectious endophthalmitis with or without pain, marked decrease in vision, diffuse corneal edema that extends limbus to limbus, photophobia, and severe anterior chamber reaction, occasionally with hypopyon. TASS presents within 12-24 hours after surgery where infectious endophthalmitis typically develops 2-7 days after surgery. Thus, new intraocular lens materials are also needed that are less inflammatory, eliminate the need for steroidal treatment, and improve or maintain ocular health.

SUMMARY

Briefly, the present disclosure provides a polymeric material comprising a polymer host; and a guest molecule comprising a glycosaminoglycan; wherein the guest molecule is disposed within the polymer host, and wherein the guest molecule is covalently bonded to at least one other guest molecule. In some embodiments, the polymer host comprises a silicone-based polymer. In other embodiments, the polymer host comprises a block copolymer. In certain aspects, the block copolymer comprising at least one polyalkylene oxide block. In some embodiments, the glycosaminoglycan is chosen from hyaluronic acid and derivatives thereof.

In some aspects, the present disclosure provides a polymeric material, comprising a polymer host comprising a silicone-based polymer; and a guest molecule comprising hyaluronic acid or derivatives thereof; wherein the guest molecule is disposed within the polymer host, and wherein the guest molecule is covalently bonded to at least one other guest molecule.

In one embodiment, the derivative of hyaluronic acid is selected from the group consisting of cetyltrimethylammonium silylhyaluronate (silyl HA-CTA), cetyltrimethylammonium hyaluronate (HA-CTA), hyaluronan salt complex $HA^{2-}QN^+$ (Formula IV), trimethylsilane-protected (TMS-protected) hyaluronan salt complex (Formula V), fluorescein-tagged hyaluronic acid, glycidyl methacrylated hyaluronic acid, and fluorescein-tagged glycidyl methacrylated hyaluronic acid.

In one embodiment, the polymeric material may be a composite.

In one embodiment, the silicone-based polymer may comprise one or more polymers selected from the group consisting of poly(dimethylsiloxane) (PDMS), poly(methylvinylsiloxane) (PVMS), and epoxidized poly(methylvinylsiloxane) (ePVMS).

In one embodiment, when the silicone-based polymer is ePVMS, the ePVMS may have an average molecular weight of 3 kDa to 40 kDa before curing.

In one embodiment, the silicone-based polymer may comprise 3% to 40% vinyl groups per repeated monomeric unit.

In one embodiment, the silicone-based polymer may be a block copolymer comprising at least one polysiloxane block and at least one polyalkylene oxide block.

In one embodiment, the silicone-based polymer may be thermostable at a temperature up to 150° C. in the absence of light having a wavelength less than 300 nm. In another embodiment, the silicone-based polymer may be thermostable at temperature up to 200° C. In another embodiment, the light may have a wavelength less than 200 nm.

In one embodiment, the silicone-based polymer may comprise 10% to 90% polysiloxane blocks by weight and 90% to 10% polyalkylene blocks by weight.

In one embodiment, the polyalkylene oxide may be polyethylene oxide (PEO). In another embodiment, the PEO may have an average molecular weight of 3 kDa to 160 kDa before curing.

In one embodiment, upon heating, the polymer host may form domains of the at least one polysiloxane block and of the at least one polyalkylene oxide block that are substantially co-continuous with domain sizes from about 5 nm to about 30 nm.

In one embodiment, the polymeric material may be a hydrogel.

In one embodiment, the polymeric material may have a surface wettability characterized by a contact angle of between 40° and 160°, such as between 80° and 130°, or between 100° and 115°.

In one embodiment, the percentage of covalently bonded guest molecules within the polymer host may be 0.2% to 3.5% by weight.

In one embodiment, the concentration of the guest molecule in the polymeric material may be greater at a surface of the polymer host than at a core of the polymer host.

In one embodiment, the average molecular weight of the covalently bonded guest molecule may be 0.75 kDa to 10 kDa.

In one embodiment, the polymeric material may resist protein adsorption compared to the polymer host without the guest molecule disposed therein.

In one embodiment, the polymeric material may retain preocular tear film compared to the polymer host without the guest molecule disposed therein.

In one embodiment, the spread of mucin onto a cornea may be enhanced compared to the polymer host without the guest molecule disposed therein.

In one embodiment, light transmission may not be substantially diminished compared to the polymer host without the guest molecule disposed therein.

In one embodiment, a surface of the polymeric material may be patterned with covalently-attached hyaluronic acid using ultraviolet exposure.

In other aspects, the present disclosure provides a polymeric material, comprising polymer host comprising a block copolymer comprising at least one polyalkylene oxide domain; and a guest molecule comprising hyaluronic acid or derivatives thereof; wherein the guest molecule is disposed within the polymer host, and wherein the guest molecule is covalently bonded to at least one other guest molecule.

In one embodiment, polyalkylene oxide may be polyethylene oxide (PEO). In one embodiment, the PEO may have an average molecular weight of 3 kDa to 160 kDa before curing. In one embodiment, the block copolymer may be a polystyrene-polyethylene oxide (PS-PEO) block copolymer or a poly(ethyl ethylene)-polyethylene oxide (PEE-PEO) block copolymer.

In one embodiment, the block copolymer may further comprise at least one polysiloxane block. In one embodiment, the at least one polysiloxane block comprises one or more polymers selected from the group consisting of poly(dimethylsiloxane) (PDMS), poly(methylvinylsiloxane) (PVMS), and epoxidized poly(methylvinylsiloxane) (ePVMS). In one embodiment, the at least one polysiloxane block may be ePVMS, and the ePVMS may have an average molecular weight of 3 kDa to 40 kDa before curing.

In one embodiment, the polymer host may be thermostable at a temperature up to 150° C., such as up to 200° C., in the absence of light having a wavelength less than 300 nm, such as less than 200 nm. In one embodiment, the polymer host may comprise 10% to 90% polysiloxane blocks by weight and 90% to 10% polyalkylene oxide blocks by weight. In one embodiment, upon heating, the polymer host may form domains of the at least one polysiloxane block and of the at least one polyalkylene oxide block that are substantially co-continuous with domain sizes from about 5 nm to about 30 nm.

In other aspects, the present disclosure provides a device formed from any polymeric material described herein. The device may be a contact lens, comprising a lens body formed from the polymeric material disclosed herein; wherein the lens body is washed to remove extractable material from the lens body, and is hydrated with an aqueous liquid.

In one embodiment, the contact lens may be a silicone hydrogel contact lens.

In one embodiment, the lens body may have an oxygen permeability, a water content, a surface wettability, a modulus, and a design effective in facilitating ophthalmically compatible wearing of the contact lens by the lens wearer at least for 30 days, such as for at least 60 days.

In one embodiment, the lens body may have an oxygen permeability of at least about 50 barrers. In one embodiment, the lens body may have an oxygen permeability of at least about 120 barrers. In one embodiment, the lens body may have an ionoflux of no greater than about $5 \times 10^{-3}$ mm$^2$/min.

In yet other aspects, the present disclosure provides an intraocular implant, comprising an optic part, comprising a lens formed from any polymeric material described herein; and a haptic part comprising two support loops arranged opposite each other, for supporting the optic part, on both sides of the latter, in anterior chamber of an eye.

In one embodiment, the lens may have a thickness which increases generally from its optical axis toward its periphery, the latter then having an edge of relatively large thickness.

In one embodiment, the lens may be a diverging corrective lens. In another embodiment, the diverging corrective lens may provide a minus optical power. In another embodiment, the diverting corrective lens is a biconcave lens.

In one embodiment, the lens may be a converging corrective lens. In another embodiment, the converging corrective lens may provide a plus optical power.

In one embodiment, the device may be a knee meniscus.

In one embodiment, the device may be a spinal disk.

BRIEF DESCRIPTION OF THE DRAWINGS

In addition to the exemplary aspects and embodiments described above, further aspects and embodiments will become apparent by reference to the drawings and by study of the following descriptions.

DETAILED DESCRIPTION

Figure 1:
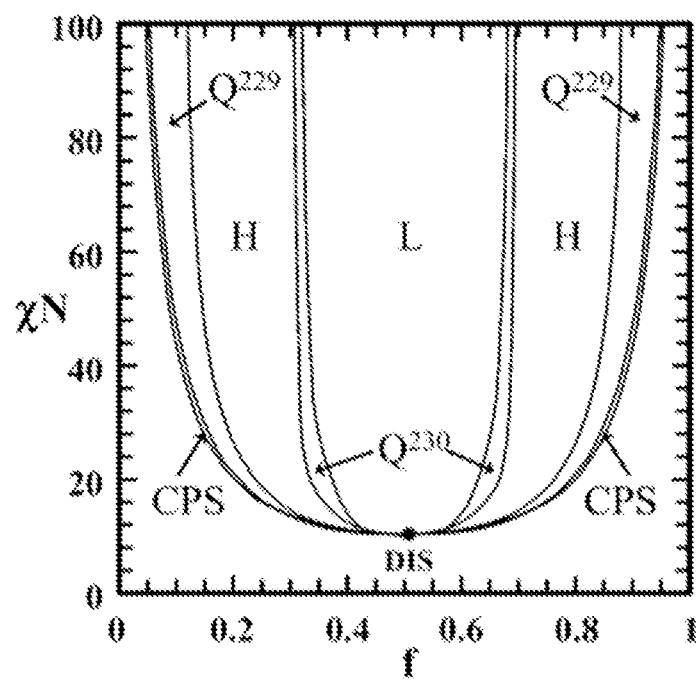
FIG. 1 shows a theoretical phase diagram showing a thermal heat trajectory (dashed arrow) involving multiple phase changes.

The present disclosure may be understood by reference to the following detailed description, taken in conjunction with the drawings as described above.

In some aspects, the present disclosure provides a polymeric material comprising a polymer host; and a guest molecule comprising a glycosaminoglycan; wherein the guest molecule is disposed within the polymer host, and wherein the guest molecule is covalently bonded to at least one other guest molecule. In some embodiments, the polymer host comprises a silicone-based polymer. In other embodiments, the polymer host comprises a block copolymer. In certain aspects, the block copolymer comprising at least one polyalkylene oxide block. In some embodiments, the glycosaminoglycan is chosen from hyaluronic acid and derivatives thereof.

In some aspects, the present disclosure provides a polymeric material, comprising a polymer host comprising a silicone-based polymer; and a guest molecule comprising hyaluronic acid or derivatives thereof; wherein the guest molecule is disposed within the polymer host, and wherein the guest molecule is covalently bonded to at least one other guest molecule.

In an alternative embodiment, the present disclosure provides a polymeric material, comprising polymer host comprising a block copolymer comprising at least one polyalkylene oxide domain; and a guest molecule comprising hyaluronic acid or derivatives thereof; wherein the guest molecule is disposed within the polymer host, and wherein the guest molecule is covalently bonded to at least one other guest molecule.

In some aspects, the present disclosure provides polymeric materials suitable for ophthalmic applications. For example, the host polymer may be a polydimethylsiloxane (PDMS)-based silicone, and the polymeric material may be formed into a device, such as a contact lens specifically designed to address the issues related to ocular surface health or TASS. In particular embodiments, silicone-based polymer of the polymer host may be modified with a guest molecule, such as hyaluronan (HA), in a manner that does not substantially change its mechanical or optical properties of the polymer host, but makes the ocular or ophthalmic device much more hydrophilic and reduces the potential for inflammatory responses associated with an ophthalmic disorder, such as TASS.

Without wishing to be bound by theory, HA plays a role in ocular health and potentially reduces protein adsorption on the polymeric materials disclosed herein. The property of reduced protein adsorption on the polymeric materials is advantageous for ocular devices, such as contact lenses and intraocular implants, formed from those polymeric materials. In one embodiment, the polymeric material may present mobile HA molecules at the surface of the polymeric material. Such as configuration may provide a durable modification suitable for various devices, such as permanent intraocular lenses and long-wearing contact lenses.

The manufacturability of polymeric materials and the ability to control composition and shape of those polymeric materials are demonstrated herein. The synthesis and manufacturing processes are developed herein and the resulting products are characterized for compositional consistency and control herein. The hydrophilicity and optical transparency of the polymeric materials are characterized herein using aqueous contact angles and light transmission measurements. Protein absorption and inflammatory potential of the polymeric materials are studied herein using in vitro cell culture techniques. Protein adsorption, monocyte adhesion and differentiation are evaluated herein on polymeric materials and on the unmodified polymer hosts.

In another aspect, the polymer host may be a block copolymer comprising a block copolymer comprising at least one polyalkylene oxide block and at least one polysiloxane block. In certain aspects, the silicone-based polymer of the polymer host may be a block copolymer comprising at least one polyalkylene oxide block and at least one polysiloxane block. In one embodiment, the polysiloxane block may be a crosslinkable polysiloxane. In another embodiment, the polyalkylene block may be a hydrophilic block. Suitable examples of hydrophilic blocks include, but are not limited to, poly(ethylene oxide), poly(glycidol), or a random copolymers of those two. In one embodiment, multiple blocks of the same type form domains within the polymer host. Without wishing to be bound by theory, the block copolymer architecture of the polymer host upon heating may undergo a self-assembly process, creating a morphology in which the hydrophobic siloxane domains and hydrophilic domains are substantially co-continuous with domain sizes limited to about 5 nm to about 30 nm.

Also without wishing to be bound by theory, the crosslinking chemistry allows the block copolymer to be provided the thermal energy sufficient for the self-assembly and for the polymer host to be processed, for example up to a temperature of about 150° C., or up to a temperature of about 200° C. In one embodiment, the siloxane domains of the block copolymer may then be ultraviolet (UV)-crosslinked to fix the morphology and macroscopic shape of the polymer host. Some room-temperature UV crosslinking chemistries may be problematic because they are also susceptible to heat, and allow the curing step to compete with, and thus disrupt, self-assembly and constrain processing to short durations. In one embodiment, the polymer host may further comprise photoinitiators. The photoinitiators may comprise onium salts, which are very thermally stable. These photoinitiators may allow the heating to take place up to 150-200° C., which is a higher temperature than typically needed to provide thermal energy sufficient for curing and crosslinking.

In one embodiment, the guest molecule is HA, and the UV-curable approach first modifies the HA disposed within the polymer host with UV-curable functional groups such that the crosslinking can be controlled using patterned UV-exposure or localized UV-exposure. For example, in one embodiment, the guest molecule is a UV-curable glycidyl methacrylate (GM) modified HA. In one embodiment, UV patterning may be used to cure HA at certain parts of the surface of the polymeric material. For example, in one embodiment, the surface of the polymeric material at its perimeter if modified optical clarity or oxygen permeability, for example, are desired.

Generally, the contact lens and intraocular lens markets are very large, and long-lasting HA-modified silicone lenses combine the benefits of silicone (e.g., oxygen permeability, low bulk water absorption, handling properties, and durability) and with the benefits of HA (lubricity, wettability, reduced foreign body response). In one embodiment, the manufacturing approach described herein results in much more durable HA content within the polymeric material than is achieved with prior art surface modification and crosslinking approaches alone.

Additional embodiments and features are set forth in part in the description that follows, and in part will become apparent to those skilled in the art upon examination of the specification, or may be learned by the practice of the embodiments discussed herein. A further understanding of the nature and advantages of certain embodiments may be realized by reference to the remaining portions of the specification the drawings, the chemical structures, and descriptions, which forms a part of this disclosure. Any description of any R-group or chemical substituent, alone or in any combination, may be used in any chemical Formula described herein, and Formulae include all conformational and stereoisomers, including diastereomers, epimers, and enantiomers. Moreover any feature of a polymeric material disclosed herein may be used in combination with any other feature of a polymeric material disclosed herein, including but not limited to the physical properties of the polymer host, properties of the guest molecule disposed therein or thereupon, or any intermediate structures, metastructures or combinations between the polymer host and the guest molecule.

I. Polymeric Material

In some aspects, the present disclosure provides a polymeric material comprising a polymer host; and a guest molecule comprising a glycosaminoglycan; wherein the guest molecule is disposed within the polymer host, and wherein the guest molecule is covalently bonded to at least one other guest molecule. In some embodiments, the polymer host comprises a silicone-based polymer. In other embodiments, the polymer host comprises a block copolymer. In certain aspects, the block copolymer comprising at least one polyalkylene oxide block.

In some aspects, the present disclosure provides a polymeric material, comprising a polymer host comprising a silicone-based polymer; and a guest molecule comprising hyaluronic acid or derivatives thereof; wherein the guest molecule is disposed within the polymer host, and wherein the guest molecule is covalently bonded to at least one other guest molecule.

In other aspects, the present disclosure provides a polymeric material, comprising polymer host comprising a block copolymer comprising at least one polyalkylene oxide domain; and a guest molecule comprising hyaluronic acid or derivatives thereof; wherein the guest molecule is disposed within the polymer host, and wherein the guest molecule is covalently bonded to at least one other guest molecule.

In one embodiment, the guest molecule disposed within the polymer host forms an interpenetrating network with the polymer host. In one embodiment, the guest molecule disposed within the polymer host forms a partial or semi-interpenetrating network with the polymer host. In one embodiment, the guest molecule disposed within the polymer host forms a dopant within the polymer host. In one embodiment, the guest molecule disposed within the polymer host is covalently bonded to the polymer host. In one embodiment, the guest molecule disposed within the polymer host forms a composite with the polymer host. In one embodiment, the guest molecule disposed within the polymer host forms a microcomposite with the polymer host. In one embodiment, the guest molecule disposed within the polymer host is crosslinked at the surface of the polymer host.

The polymeric material may comprise a composite. In some aspects, the polymeric material may be an interpenetrating polymer network (IPN), which is an intermingling of protected guest molecule and a polymer host, wherein molecules of the guest have been crosslinked with each other. A "composite" as used herein describes a material network where at least two polymer components are physically associated by being covalently linked. In general, in an IPN, at least one component is synthesized or crosslinked in the presence of the other, although the two components may be bound together. Semi-IPNs fall within the category of IPNs and, thus, composites. The interpenetration many occur at the nanometer scale, the micron scale, or both. "Microcomposite" refers to a composite where the interpenetration of the guest molecule is substantially on the micron scale, but does not preclude interpenetration and crosslinking on the nanometer scale. The term "composite" does not limit the scale on which the polymer host and the guest molecule interact with each other, nor does it limit the percentage (by volume or weight) or one component relative to the other.

Within the polymeric material, the several curing events may occur in a stepwise or simultaneous fashion. The polymer host may be cured, forming crosslinks to monomers within itself. The guest molecule may be cured, forming crosslinks to itself or to the polymer host. The polymeric material, particularly when it is a BCP, may undergo a second photochemically-initiated curing event before or after introduction of the guest molecule. In one embodiment, the polymer host may be cured, the guest molecule disposed within the cured polymer host, then the guest molecule may be cured (i.e., crosslinked). In one embodiment, the guest molecule disposed within the polymer host, and then the polymer host may be cured.

(a) Polymer Host

In one embodiment, the polymer host may be directly molded, cured in the mold, and formed with a guest molecule. In alternative embodiments, the polymer host may be first cured and formed and then swollen to form micropores that the guest molecule can diffuse into before crosslinking to itself. In one embodiment, the polymer host may be shaped using a variety of techniques and methods, including thermal curing, photocuring with, for example, ultraviolet light or other forms of radiation, casting, spin casting, blow molding, forming from a virgin resin, machining or lathing.

As used herein in the context of polymer hosts and block copolymers, unless otherwise indicated, "molecular weight"

refers to the molecular weight of the starting materials before the component are cured and/or crosslinked to each other or to form a covalent network. As such, the components of the polymer hosts or block copolymers may be selected based on their molecular weights to provide polymeric materials with certain physical and chemical properties. Thus, in this context and unless otherwise indicated, "before curing" refers to the components of the polymer host or the block copolymer as used in preparation of the polymeric material before further curing, polymerization, or crosslinking takes place.

In certain embodiments, the polymer host may comprise any silicone-based polymer with mechanical properties suitable to the material's application. Examples of suitable polymer hosts include, but are not limited to, polydimethylsiloxane (PDMS), poly(methylvinyl siloxane) (PVMS), epoxidized poly(methylvinyl siloxane) (ePVMS), and any combinations thereof. The components of the polymer host may form a covalent network with each other, the extent of which may be controlled by the degree and amount of curing.

In one embodiment, the silicone-based polymer is ePVMS. In one embodiment, the ePVMS may have an average molecular weight of 3 kDa to 40 kDa before curing. For example, the ePVMS may have an average molecular weight from about 3 kDa to about 5 kDa, from about 5 kDa to about 10 kDa, from about 10 kDa to about 15 kDa, from about 15 kDa to about 20 kDa, from about 20 kDa to about 25 kDa, from about 25 kDa to about 30 kDa, from about 30 kDa to about 35 kDa, or from about 35 kDa to about 40 kDa before curing. In one embodiment, the ePVMS may have an average molecular weight of greater than about 3 kDa before curing. In one embodiment, the ePVMS may have an average molecular weight of less than 40 kDa before curing.

In one embodiment, the silicone-based polymer may comprise 3% to 40% vinyl groups per repeated monomeric unit. The concentration of vinyl groups per repeated monomeric unit can and will vary. In one embodiment, the silicone-based polymer may comprise from about 3% to about 5%, from about 5% to about 10%, from about 10% to about 15%, from about 15% to about 20%, from about 20% to about 25%, from about 25% to about 30%, from about 30% to about 35%, or from about 35% to about 40% vinyl groups per repeated monomeric unit.

In some embodiments, the polymer host may have an average thickness of about 25 µm to about 100 µm, for example about 25 µm to about 30 µm, about 30 µm to about 35 µm, about 35 µm to about 40 µm, about 40 µm to about 45 µm, about 45 µm to about 50 µm, about 50 µm to about 55 µm, about 55 µm to about 60 µm, about 60 µm to about 65 µm, about 65 µm to about 70 µm, about 70 µm to about 75 µm, about 75 µm to about 80 µm, about 80 µm to about 85 µm, about 85 µm to about 90 µm, about 90 µm to about 95 µm, about 95 µm to about 100 µm. In a particular embodiment, the film is about 50 µm thick. In one embodiment, the polymer host may have an average thickness of about 1 mm to about 5 mm, such as from about 1 mm to about 2 mm, from about 2 mm to about 3 mm, from about 3 mm to about 4 mm, or from about 4 mm to about 5 mm.

(b) Block Copolymers

In various embodiments the polymer host may comprise a block copolymer (BCP). In certain embodiments, the block copolymer comprising at least one polyalkylene oxide block. In one embodiment, the silicone-based polymer may be a block copolymer comprising at least one polysiloxane block and at least one polyalkylene oxide block.

In one embodiment, thermally stable photocuring chemistry is integrated into high impact block copolymer melt systems, enabling facile and selective trapping of an expressed microphase separated morphology at any temperature. In one embodiment, the polymer host may be exposed to extended thermal processing conditions (<150° C.) without inducing premature cure; that is, the curing event may be triggered only upon the exposure of the sample to externally applied UV light (<300 nm). In other words, the polymer host is thermostable at a temperature up to at least about 150° C., such as up to at least about 200° C.

In one embodiment, the ability to divorce thermal processing and curing events in BCP systems transforms capacity to fix morphology outside of a BCP's thermodynamically determined melt phase boundaries.

In one embodiment, the polymer host (e.g., the silicone-based polymer or block copolymer) may be thermostable at a temperature up to 150° C. in the absence of light having a wavelength less than 300 nm. In another embodiment, the silicone-based polymer may be thermostable at temperature up to 200° C. In another embodiment, the light may have a wavelength less than 200 nm.

In one embodiment, the silicone-based polymer may comprise from about 10% to about 90% polysiloxane blocks by weight. For example, the silicone-based polymer may comprise polysiloxane blocks from about 10% to about 20% by weight, from about 20% to about 30% by weight, from about 30% to about 40% by weight, from about 40% to about 50% by weight, from about 50% to about 60% by weight, from about 60% to about 70% by weight, from about 70% to about 80% by weight, or from about 80% to about 90% by weight.

In one embodiment, the silicone-based polymer may comprise greater than about 10% polysiloxane blocks by weight.

In one embodiment, the silicone-based polymer may comprise less than about 90% polysiloxane blocks by weight.

In one embodiment, the silicone-based polymer may comprise from about 90% to about 10% polyalkylene blocks by weight. For example, the silicone-based polymer may comprise polyalkylene blocks from about 10% to about 20% by weight, from about 20% to about 30% by weight, from about 30% to about 40% by weight, from about 40% to about 50% by weight, from about 50% to about 60% by weight, from about 60% to about 70% by weight, from about 70% to about 80% by weight, or from about 80% to about 90% by weight.

In one embodiment, the silicone-based polymer may comprise greater than about 10% polyalkylene blocks by weight.

In one embodiment, the silicone-based polymer may comprise less than about 90% polyalkylene blocks by weight.

In one embodiment, the silicone-based polymer may comprise 10% to 90% polysiloxane blocks by weight and 90% to 10% polyalkylene blocks by weight.

In one embodiment, the polyalkylene oxide may be polyethylene oxide (PEO).

In another embodiment, the PEO may have an average molecular weight of 3 kDa to 160 kDa before curing. For example, the PEO may have an average molecular weight from about 3 kDa to about 5 kDa, from about 5 kDa to about 10 kDa, from about 10 kDa to about 15 kDa, from about 15 kDa to about 20 kDa, from about 20 kDa to about 25 kDa, from about 25 kDa to about 30 kDa, from about 30 kDa to about 35 kDa, from about 35 kDa to about 40 kDa from about 40 kDa to about 45 kDa, from about 45 kDa to about 50 kDa, from about 50 kDa to about 55 kDa, from about 55 kDa to about 60 kDa, from about 60 kDa to about 65 kDa, from about 65 kDa to about 70 kDa, from about 70 kDa to about 75 kDa, from about 75 kDa to about 80 kDa, from about 80 kDa to about 85 kDa, from about 85 kDa to about 90 kDa, from about 90 kDa to about 95 kDa, from about 95 kDa to about 100 kDa, from about 100 kDa to about 105 kDa, from about 105 kDa to about 110 kDa, from about 110 kDa to about 115 kDa, from about 115 kDa to about 120 kDa, from about 120 kDa to about 125 kDa, from about 125 kDa to about 130 kDa, from about 130 kDa to about 135 kDa, from about 135 kDa to about 140 kDa, from about 140 kDa to about 145 kDa, from about 145 kDa to about 150 kDa, from about 150 kDa to about 155 kDa, or from about 155 kDa to about 160 kDa before curing.

In one embodiment, the PEO may have an average molecular weight of greater than about 3 kDa before curing.

In one embodiment, the PEO may have an average molecular weight of less than 160 kDa before curing.

In one embodiment, upon heating, the polymer host may form domains of the at least one polysiloxane block and of the at least one polyalkylene oxide block that are substantially co-continuous with domain sizes from about 5 nm to about 30 nm. For example, the domains may have sizes of about 5 nm, about 6 nm, about 7 nm, about 8 nm, about 9 nm, about 10 nm, about 11 nm, about 12 nm, about 13 nm, about 14 nm, about 15 nm, about 16 nm, about 17 nm, about 18 nm, about 19 nm, about 20 nm, about 21 nm, about 22 nm, about 23 nm, about 24 nm, about 25 nm, about 26 nm, about 27 nm, about 28 nm, about 29 nm, or about 30 nm. In one embodiment, the domain size may be greater than about 5 nm. In another embodiment, the domain size may be less than 30 nm.

As an illustrative example, and without wishing to be bound by theory, consider a sample that sits along the dashed line within the theoretical phase diagram for an AB diblock copolymer melt. In FIG. 1, f represents the volume fraction of block A, and $\chi N$ is an order parameter that is inversely related to temperature (through $\chi$) and directly proportional to molecular size (N). At lower temperatures (high values of $\chi N$) the BCP adopts the lamellar morphology (L). Upon heating, it proceeds through multiple ordered states, including the gyroid (aka $Q^{230}$) and hexagonal morphologies (H), before finally disordering into an isotropic fluid (DIS). Such complex behavior has been experimentally observed in many BCP systems. One such example is included in FIG. 1, where transitions between the lamellar ($L_c$ and L), modulated lamellar (metastable) (ML), gyroid (aka $Q_{Ia3d}$), and hexagonal (H) phases in a poly(ethyl ethylene-b-ethylene oxide) (PEE-PEO) BCP are shown as a function of temperature using rheological changes in the elastic modulus (G').

As with most BCP systems and without wishing to be bound by theory, solidification is used in many, if not most, proposed applications, such as separation membranes, lithographic masks, biomedical devices, tissue scaffolds, etc. In the example given in FIG. 1, cooling the sample to room temperature employs (1) a transition to the lamellar phase, and (2) crystallization of the PEO. The former prohibits trapping any morphology other than the lamellar phase, while the second event is disruptive to any long-range order processed into the system. In contrast, having the ability to trigger a curing event at any temperature allows one to (1) trap any morphology present along such a thermal trajectory and (2) suppress the disruptiveness of additional thermal transitions, such as crystallization, from permanently destroying the morphology.

In various embodiments, BCP systems may include judiciously integrate cationically polymerizable epoxide groups, which, when combined with thermally stable onium photoacid generators, can be rapidly cured at any temperature (<150° C. or <200° C.) upon exposure to sub-300 nm light. In one embodiment, the thermal stability of the sulfonium photoacids, together with the rapid cure kinetics associated with the cationic polymerization mechanism, minimizes morphological changes during cure.

In one embodiment, polysiloxane-based BCPs are flexible, thermally stable, and exhibit very low glass transition temperatures of about −150° C. to about −10° C. (depending upon the substituents) and may be crosslinked. In one embodiment, homopolymer (or oligomer) derivatives of this BCP may be used for thermally curable and photocurable elastomer resins and adhesives applied as coatings, thin films, lithographic resists, medical consumables, biomedical and microfluidic devices, and in biological microelectromechanical (BioMEMS) applications.

These strategies may be applicable to any polymer host comprising BCPs in which cationically polymerizable groups can be introduced into at least one block. In this regard, and in some embodiments, the two systems targeted may represent the extremes with respect to the synthetic complexity: The polydiene systems are amenable to chemical modification under a wide range of reaction conditions, while the polysiloxane systems are sensitive to moderately basic conditions and must be handled accordingly.

In one embodiment, the developed polysiloxane BCPs may be used as precursors to nanostructured free-standing films of selected morphologies, and, as covalently integrated surface modifiers, to existing polysiloxane-based epoxy resins.

In one embodiment, the robust (permanent) modification of the resin surfaces with BCP structures is contingent on two principal conditions. One must not only be able to chemically fix the BCP layer in the desired morphology at the surface as proposed, but must simultaneously achieve covalent attachment between the BCP layer and the resin surface.

In one embodiment, the chemical modifications of the polysiloxane BCPs are directly compatible with the classic polysiloxane resin curing chemistry, such as metal-catalyzed hydrosilylation. In one embodiment, covalently adhering the BCP layer on these commercial systems is straightforward when the layer is introduced during the mid to late stages of cure.

Figure 2:
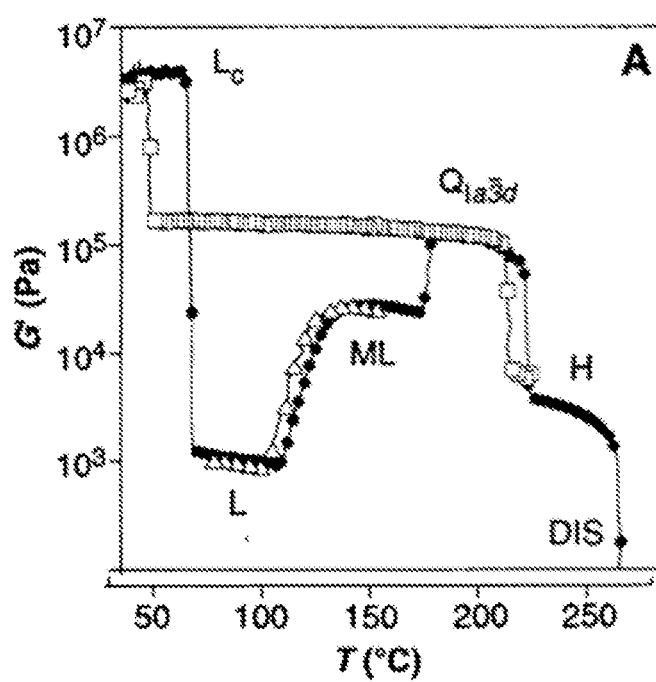
FIG. 2 shows an experimental confirmation of complex behavior in a poly(ethyl ethylene-b-ethylene oxide) (PEE-PEO) sample involving a thermal heat trajectory involving multiple phase changes.

In contrast to small molecule, single polymer layer, or plasma-based modification strategies, in some embodiments, the photocurable BCP systems may permit direct access to hierarchical surface patterning. That is, a combination of masks and temperature changes can be used to controllably photopattern the BCP with different morphologies directly onto the surface (FIG. 2, and Example 6 below). In one embodiment, the secondary block also provides access to much higher concentrations of integrated functional groups than is possible with single layer modifications if, for example, the secondary block can be solvated by the interfacing medium.

In one embodiment, many secondary blocks may demonstrate morphological trapping, providing a generic platform through which incorporation of a wide range of block choices is possible. In one embodiment, the synthetic routes provided herein may create epoxide-containing blocks with high end group functionalities, functionalities which allow for subsequent addition of the secondary block through either reinitiated chain growth, or coupling strategies, whichever may be appropriate to the block type desired.

For example, in some embodiments, BCPs may introduce hydrophilic, biologically compatible, non-fouling character to elastomeric systems, which may be in biotechnology, microfluidic, BioMEMS, and biomedical devices. In particular embodiments, polyethylene oxide (PEO) and poly (N-isopropylacrylamide) (PNIPAM) may be introduced as secondary blocks into these systems.

In one embodiment, high efficiency methods are developed herein to produce polysiloxane-based BCPs with controlled integration of cationically curable epoxide sidegroups. Control is demonstrated herein over BCP composition, molecular weights, coupling efficiencies, as well as epoxide distribution and density within the block. Significant challenges reside around the incompatibility of standard synthetic approaches with these systems, particularly those involving polysiloxane-based blocks.

The pre- and post-cure morphological behavior is comprehensively characterized herein in selected systems over a wide range of BCP compositions. Without wishing to be bound by theory, both real-time rheological and small angle X-ray scattering (SAXS) elucidate herein the morphological and mechanical changes within these systems as a function of cure time. Epoxide and photoacid concentrations on phase behavior, the true thermal tolerance of the curing mechanism, curing kinetics and the degree to which morphology and long-range order can be preserved as a function of morphology, epoxide and photoacid content, cure time, sample thickness, age, and processing history are each assessed herein. Samples, as both free-standing films and surface modification layers on commercial resins (e.g., Sylgard 184™ (Dow Chemical)), are produced herein.

A general foundation for synthesis and direct application are provided herein for a wide range of UV-curable block copolymer systems. In many BCP systems described herein, particularly those of advanced architectures, complex morphologies have been detected in small thermal windows that limit their availability for both characterization (e.g., by electron microscopy) and application in a range of potential settings. The developed systems described herein which permit thermally insensitive photocuring provide an avenue for isolating some of these morphologies. In the past, impact of cure and rapid curing kinetics on BCP morphology and its preservation were poorly understood due to a general lack of curable BCP systems for which melt-state self-assembly could be achieved independently from the curing event. The systems described herein divorce the thermal state of the BCP from the curing trigger, allowing direct monitoring of morphological change (using combined in situ SAXS and rheology) as a function of cure time and crosslink density. Previous siloxane-based photocurable homopolymers, as well as non-curable BCPs, are both produced using synthetic schemes that rely almost exclusively on hydrosilylation coupling mechanisms. Without wishing to be bound by theory, reliance on hydrosilylation alone to incorporate photocurability into BCP architecture is problematic. The processes described herein provide alternative, orthogonal methods, which meet the growing for versatile routes to multi-functional siloxane polymer systems.

In one embodiment, the developed BCPs provide a robust method for direct surface modification (patterned and non-patterned) of existing commercial resins with a wide array of BCP-based materials.

In one embodiment, improvements in wear, biocompatibility, fouling resistance, adhesion, surface functionality, etc. of existing elastomer resins may impact a wide range of academic and commercial areas of technology development, including for example microfluidics, BioMEMs and biomedical device applications, separation and membrane technologies, and resist and coating applications.

In one embodiment, UV- and thermally curable polysiloxane homopolymer systems are already used across the commercial and academic landscapes, with a notable absence of BCPs in this regard. The absence, of course, is related directly to the prior lack of synthetic methodologies developed for the integration of these photocurable polymers into blocked architectures, which lack is overcome by the present disclosure.

Without wishing to be bound by theory, two principal strategies have been historically used to solidify or trap melt-state morphologies in BCP systems: either (1) cooling induced vitrification of or (2) melt-state crosslinking of one or more of the constituent polymer blocks; the exact strategy used being very system specific. Taken together, the collection of these established strategies share a common fundamental limitation: the mechanisms for the solidification techniques used are temperature-dependent; that is, the temperature at which the solidification mechanism can be triggered is largely fixed by the chemistry or the physical properties of the system. This limitation presents a significant challenge for generalizing solidification strategies to other BCP samples, since BCPs commonly exhibit multiple thermally induced morphological states. The temperatures at which those changes take place are a strong function of the chemical nature, size, and relative composition of the constituent blocks. The capability to selectively trap multiple, temperature-dependent morphologies from the same sample, by either of these classical strategies, has not been previously demonstrated.

For example, and without wishing to be bound by theory, simple vitrification strategies, while generally effective at producing solids of a desired morphology with little loss in melt-state organization, are constrained by the inability to preserve any morphology except that directly superior to the highest glass transition. Highly ordered BCP systems tend to also come from lower molecular weight materials, where there is limited kinetic resistance to ordering. Since these molecular weights routinely fall below those used to produce high entanglement densities, vitrification in these samples tends to yield very brittle mechanical characteristics with little resistance to solvation. Classical crosslinking strategies have been proposed as a means to overcome these some of these limitations; unfortunately, effective and efficient solutions based on thermally independent cure mechanisms, permitting selective morphological trapping, have remained scarce.

Examples of such classical crosslinking strategies applied to BCP systems include: (1) condensation or coupling reactions, (2) thermally-initiated free radical polymerizations, and (3) integrating reactive (post-polymerization) repeat units. Without wishing to be bound by theory, self-initiated condensation and coupling based mechanisms in BCPs compete with the timescales of the self-assembly process and effectively preclude any significant application of thermal processing. Catalytic coupling reactions, such as hydrosilylation reactions likewise occur upon introduction of the catalytic agent and therefore prohibit any thermal treatment. The general disadvantage of these approaches is their reliance on small molecules (catalysts, free radical initiators, coupling agents) that must be pre-integrated with the self-assembled system to evoke a homogeneous cure.

Still without wishing to be bound by theory, several more systems, in which the crosslinking molecules are introduced through vapors such as sulfur monochloride or 1,4-diiodobutane, seem to circumvent this problem, the crosslinking reaction is slow, taking up to two weeks for a full cure. As such, these methods have only been applied to samples pre-solidified through vitrification of another block. The feasibility of their application to melts is suspect given the exposure times. Thermal processing under these conditions is impractical in most cases. Crosslinking systems that use thermally-initiated free radical mechanisms can be effective, but the initiator is selected in a system specific manner, such that cure is activated in the desired thermal window. If the desired morphological window is small, the curing event initiates during the approach to the phase boundary, which can result in mixed phase solids. At the very least, thermally induced free radical initiators prohibit extended pre-cure processing in the thermal window of interest, and are therefore particularly unsuitable for systems exhibiting more complex phase behavior. At the other end of the spectrum, monomer molecules have been developed which retain latent reactive functionality post-polymerization and can then be employed to crosslink the system. The two prominent examples, benzocyclobutene and 2,3-dimethylenebicyclo[2.2.1]-heptane, both rely on thermally-induced cycloaddition reactions activated at high temperatures. As such, these systems are constrained to high temperature cures and preclude selective morphological trapping at lower temperatures.

In contrast to these vitrification and thermal curing approaches, and in one embodiment, UV-activated curing chemistries have been integrated into various BCPs systems. As with more classical approaches, any light-triggered curing mechanism applied to BCPs must also be tolerant of pre-cure thermal processing. Photo-induced free radical initiators notoriously suffer from poor thermal stability, with the exception of acylphosphineoxides that are stable up to 180° C. Unfortunately, these photoinitiators are sensitive to visible light, which makes it difficult to avoid premature curing in the system without special handling.

Figure 3:
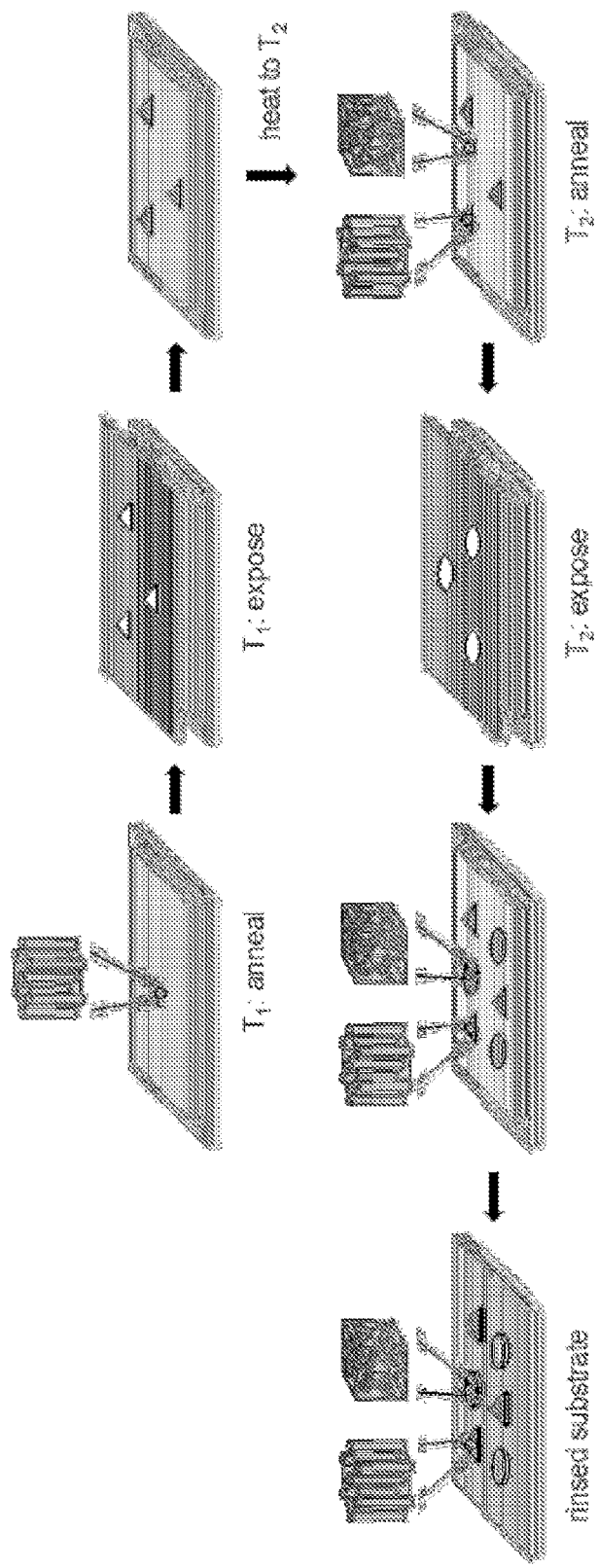
FIG. 3 shows an example of how a combination of masks and temperature changes with the developed, thermally tolerant photocurable block copolymer (BCP) systems can be used to create patterns of multiple morphological domains from a single BCP.

Alternatively, in one embodiment, photoinitiated cationic crosslinking reactions with onium salt photoacids (FIG. 3) have been shown herein to possess great thermal stability (reported to 150° C.) in epoxy functional curing systems without premature curing under extended thermal processing conditions. As such, in one embodiment, BCP systems incorporating this rapid cationically based curing chemistry afford a means of selectively trapping of any expressed morphology over a wide range of temperatures.

In one embodiment, incorporating sulfonium salts and cationically polymerizable functional groups (such as, oxiranes, vinyl ethers, thiiranes, etc.) allows for the separation of thermal processing from the curing event.

In one embodiment, the described cationic crosslinking of integrated epoxide groups forms the basis in the BCP systems. In one embodiment, polysiloxane BCPs are developed with controlled degrees of epoxidation along the olefin and siloxane main chains, which can then be UV-cured at any temperature. As an example, in one embodiment, the acid-initiated cationic curing mechanism for a partially epoxidized polydiene chain is given in FIG. 4.

Without wishing to be bound by theory, a notable advantage to this polymerization mechanism as a curing vehicle, is its propensity to form cycles through intra-chain backbiting. This tendency to eject cycles from the growing chain end provides greater degrees of freedom early in the curing process, relieving some of the constraints imposed by the standard sequential attack. Ejected cycles remain effective crosslinks, while allowing chains to rearrange. The predisposition to cyclize, in combination with the rapid kinetics of cationic oxirane polymerizations, may represent factors enabling trapping of morphology by this technique.

Without wishing to be bound by theory, the polysiloxane system presents a challenge from a synthetic standpoint. The challenge is apparent when one considers independently the current synthetic methodologies to produce (1) epoxy-functional (photocurable) polysiloxane monomers and homopolymers, and (2) end-functional polysiloxanes and polysiloxane BCPs. The current methods rely almost exclusively on hydrosilylation coupling. This creates a competitive conflict when more than one of these coupling reactions is used. For example, one cannot use hydrosilylation to both add epoxy groups to the main chain and simultaneously couple a second block exclusively to the chain end. The hydrosilylation reaction cannot distinguish between the two different reaction sites, and coupling would be uncontrollable and non-specific. As a result, efficient strategies or orthogonal methods herein are used herein for producing disclosed polymeric materials.

This discrepancy in synthetic demands between systems is used. The straightforward development of the polydiene BCP system disclosed herein allows the probing of the influence of such parameters as epoxide content, epoxide conversion, photoacid concentration, cure time, light intensity, domain structure, sample thickness, etc. on trapping performance during cure (as free standing films, as well as surface layers on commercial resins). This advantage allows characterization and definition of conditions for morphological trapping across the phase diagram while simultaneously developing the more demanding synthetic methodologies for preparing the polysiloxane analogs. These advantages are applied to any polymeric material disclosed herein.

In one embodiment, the route to epoxide-functional polysiloxanes is based on introducing pendant vinyl units to the main chain through anionic polymerization of 1,3,5-trivinyl-1,3,5-trimethylcyclotrisiloxane (D3V) (FIG. 5) to give poly(methylvinylsiloxane) or PVMS.

In one embodiment, sequential monomer addition as a means of introducing a second block is severely restricted due to the limited reactivity of the silyl oxanion towards virtually all other anionically polymerizable monomers, coupled with the unfortunate formation of a highly labile Si—O—C linkage between blocks for the few remaining possibilities (ethylene oxide, e.g.).

In one embodiment, some opportunity exists to incorporate less reactive anionically polymerizable monomers such as styrene, vinyl pyridines, and dienes by reversing the sequence of addition (D3V added second in the sequence), but as discussed above high UV absorptivities of the two former monomers is likely problematic for the efficient activation of the onium photoacids.

In one embodiment, incorporating dienes is a permutation that allows simultaneous crosslinking of both blocks. Like the polydiene macroinitiators described above, terminally functional polysiloxane molecules likewise provide an opportunity to diversify the collection of possible secondary blocks types.

Without wishing to be bound by theory, the classic method in which secondary blocks (other than those possible through sequential anionic polymerization discussed above) are introduced to non-reactive polysiloxanes such as poly (dimethylsiloxane) (PDMS), is through very efficient Pt-catalyzed hydrosilylation coupling reactions. Typically this involves terminal silane functionality on PDMS and a terminal alkene on the secondary block. In one embodiment, PDMS-PEO BCPs have been synthesized in this way. Without wishing to be bound by theory, use of hydrosilylation coupling with PVMS samples may be problematic due to the inability of the system to distinguish between vinyl groups on the terminus of the secondary block and those in the polysiloxane main chain. This issue may be circumvented if all of the vinyl groups in the PVMS chain can be converted to other functionalities before the coupling reaction is carried out. In one embodiment, epoxidation of vinyl groups in PVMS with mCPBA can carried out quantitatively, and may provide use of coupling as a means to introduce secondary blocks unavailable through other routes, such as PEO, for example.

Figure 5:
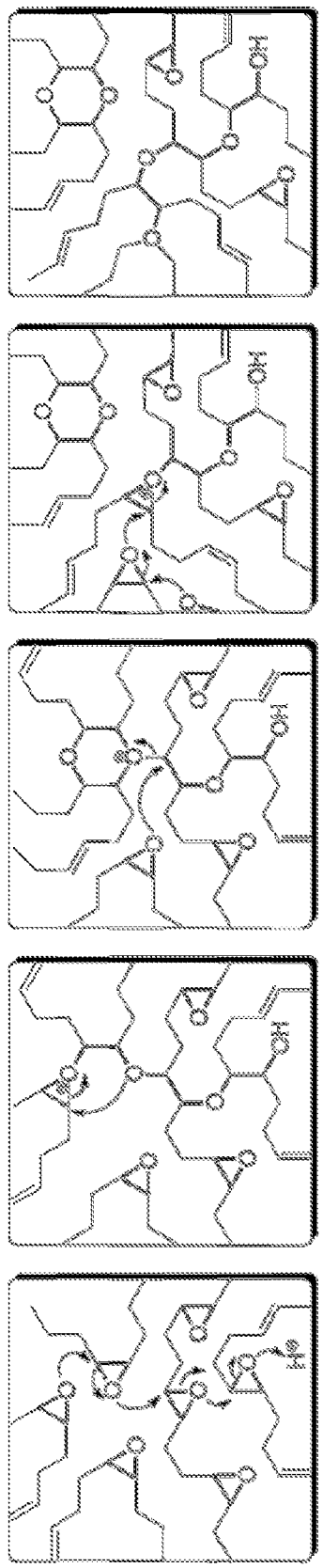
FIG. 5 shows cationic crosslinking of partially epoxidized polydiene chains, initiated by protonation of a main chain epoxide. Backbiting produces cycles that can be ejected from the growing chain end.

The effect of epoxide content on the phase behavior, cure performance, and resultant material properties are studied herein. In one embodiment, the vinyl content in the polysiloxane may be controlled to values lower than 100% (vinyl groups per repeat unit) if quantitative epoxidation is used for efficient coupling, as disclosed herein. In one embodiment, a controlled amount of vinyl content may be produced through copolymerization of D3V with D3, the non-functional monomer (FIG. 5). In one embodiment, incorporating the two monomers reflects the reaction mixture composition (25% D3V monomer, 23.4% incorporated), but may be too blocky in nature due to the mutual preference of the growing chain to incorporate the more reactive of D3V monomer first. This block structure may still allow use of these blocks in photocuring applications, but may lead to inhomogeneous distributions of crosslink density within the polysiloxane domains.

Figure 7:
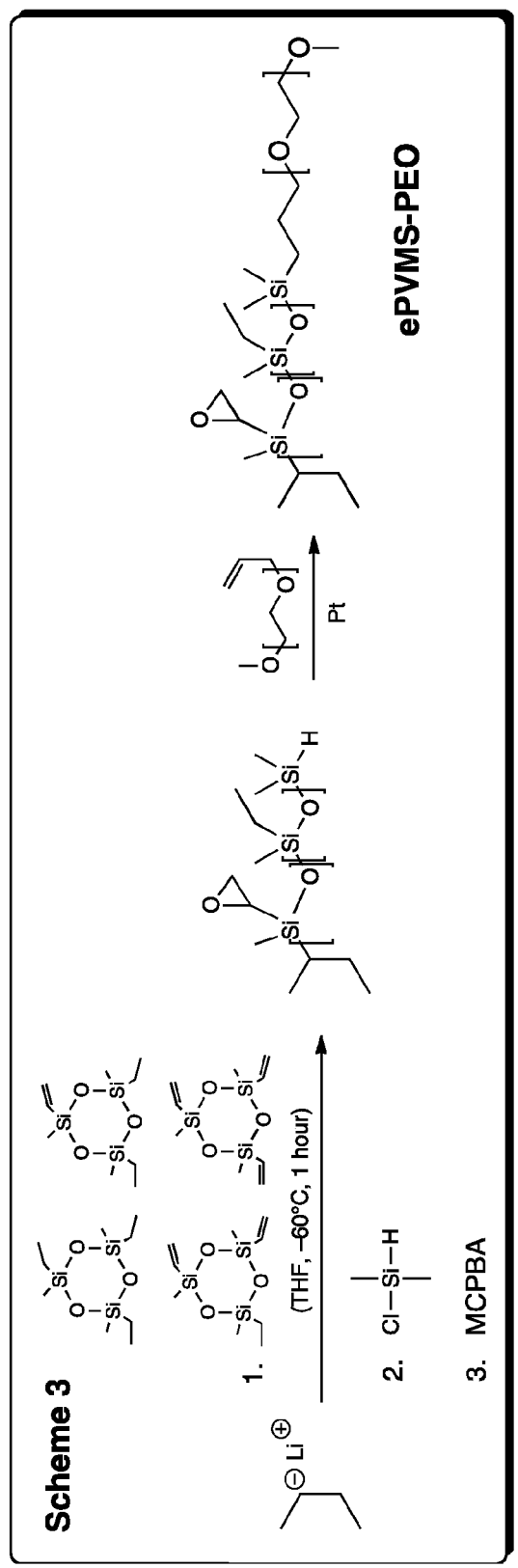
FIG. 7 gives a sample route towards a silane-terminated poly(methylvinyl siloxane) (PVMS) homopolymer prepared for subsequent coupling with a second, alkene functional block, such as polyethylene oxide (PEO).

In one embodiment, a more statistical distribution of the vinyl functional repeat units may be possible through the partial hydrogenation of the D3V monomer with reagents such as para-toluenesulfonylhydrazide, which can be carried out in the liquid phase and allows direct use of stoichiometry with respect to alkene groups present to control the degree of hydrogenation. The result may be a polymerizable mixture of D3V derivatives (hD3V) with varying vinyl group content. In FIG. 7, Scheme 3 gives an exemplary route towards a silane-terminated PVMS homopolymer prepared for subsequent coupling with a second, alkene functional block (e.g., PEO), in which such a blend of monomer derivatives is used.

In one embodiment, some homopolymer contamination is present in BCP samples produced through coupling reactions. In one embodiment, it is often possible (though far from ideal) to remove unwanted homopolymer through equilibrium-based (read inefficient) fractionation, but in this case is likely unnecessary. In one embodiment, such contamination in and of itself does not preclude the formation of highly ordered BCP morphologies if concentrations are kept moderate (<30%).

In one embodiment, such an approach may be warranted in cases where coupling is the only option, which is the case for PVMS-PEO, a highly valuable target for the biomedical, microfluidics, and BioMEMs application areas.

In one embodiment, versatile PVMS macroinitiators may be produced which are analogous to the polydiene macroinitiators outlined above.

In one embodiment, one challenge in functionalizing anionically polymerized siloxanes is that the functional group must be introduced without forming Si—O—C bonds that are highly labile unless sterically hindered. Thus terminating agents may be fashioned to avoid this instability, which is commonly accomplished through terminating agents that produce Si—O—Si—C-bond sequences. Likewise, efficient introduction of terminal functional groups through reactive terminating agents may use functional groups in a protected, non-reactive form.

Figure 8:
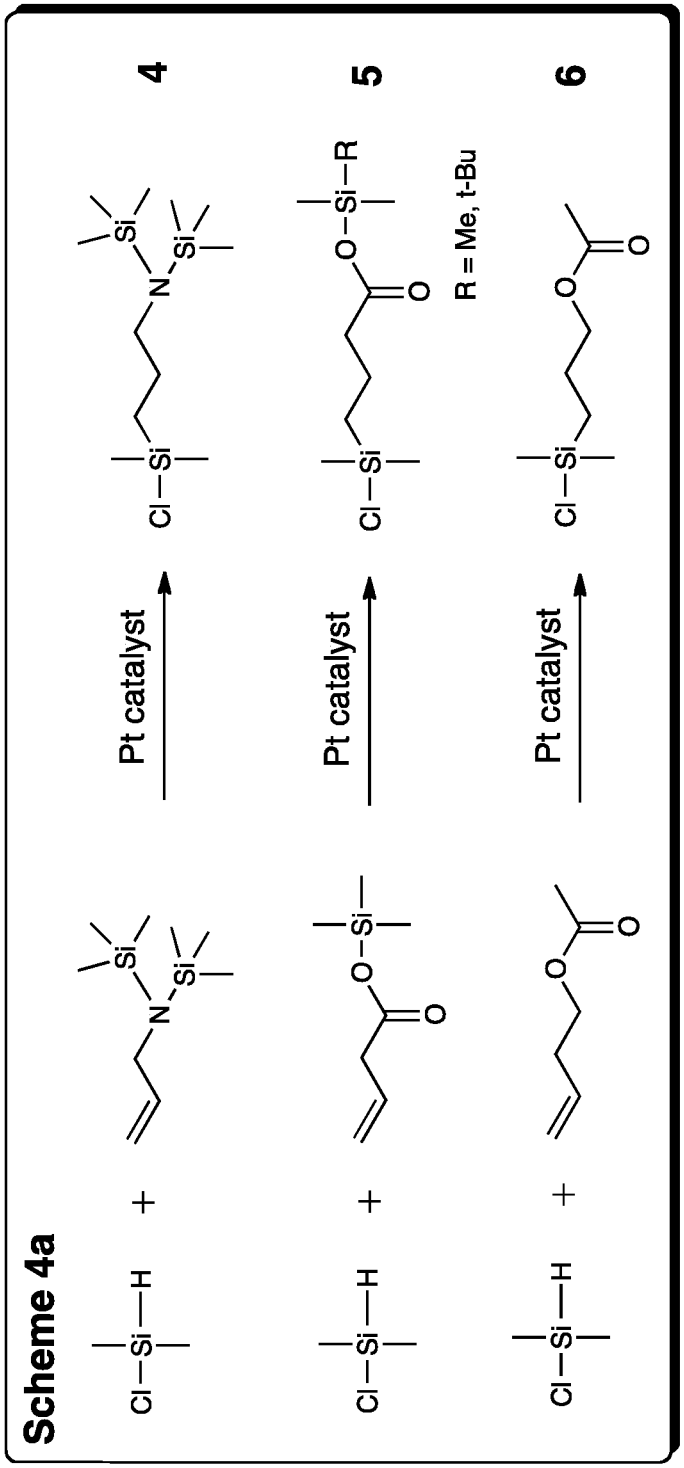
FIG. 8 depicts reaction with a tert-butyldimethylsilane (TBDMS)-protected organolithium initiator.
Figure 9:
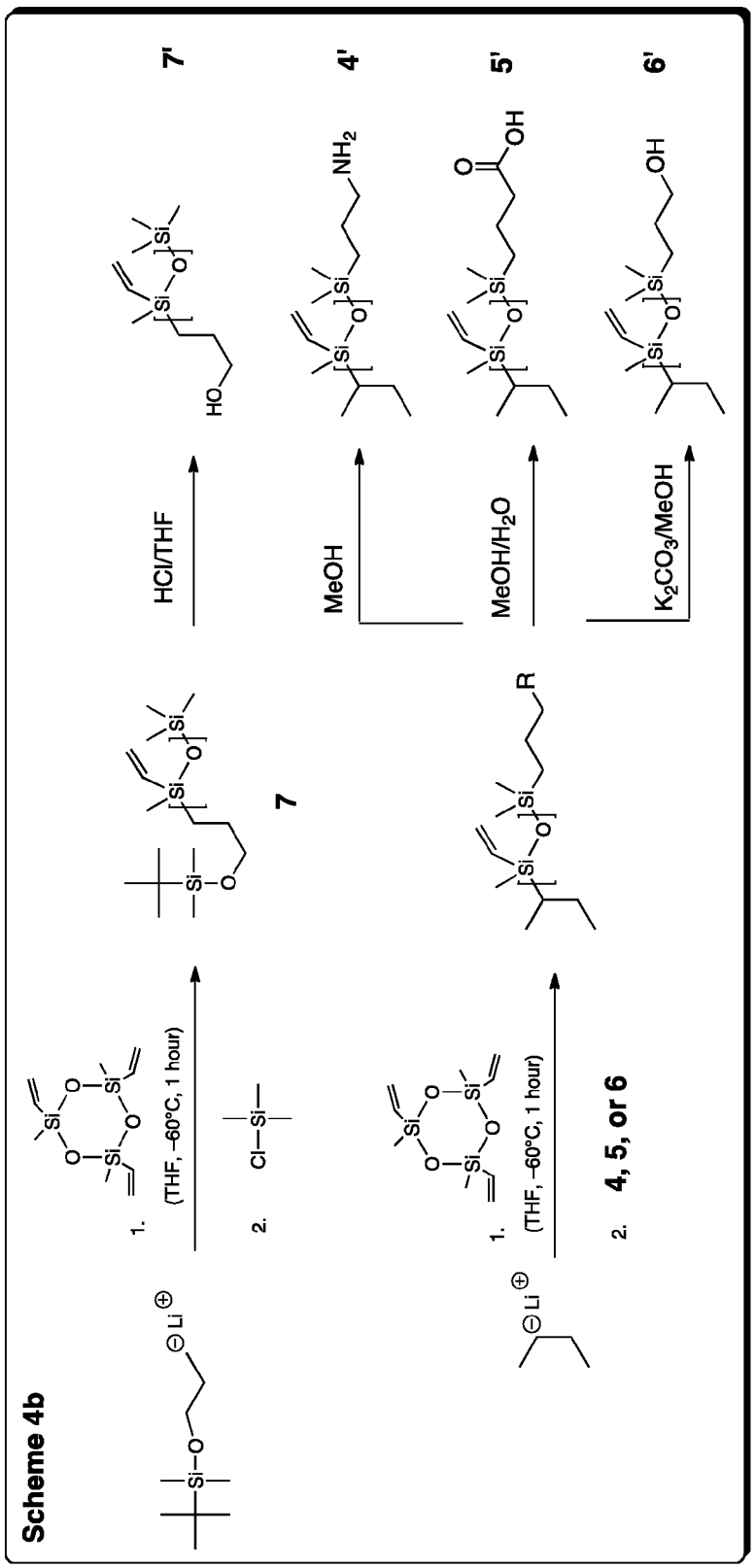
FIG. 9 depicts the synthesis of several suitable terminating agents with mild deprotection protocols compatible with polysiloxane systems described herein.
Figure 10:
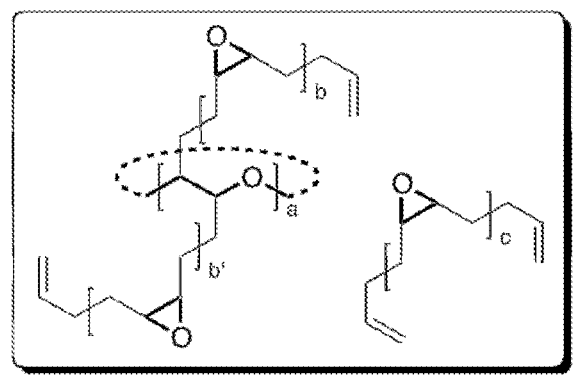
FIG. 10 generically represents degradation products from the cross-metathesis of the cured polydiene products with ethylene gas. Some products may be cyclics.
Figure 11:
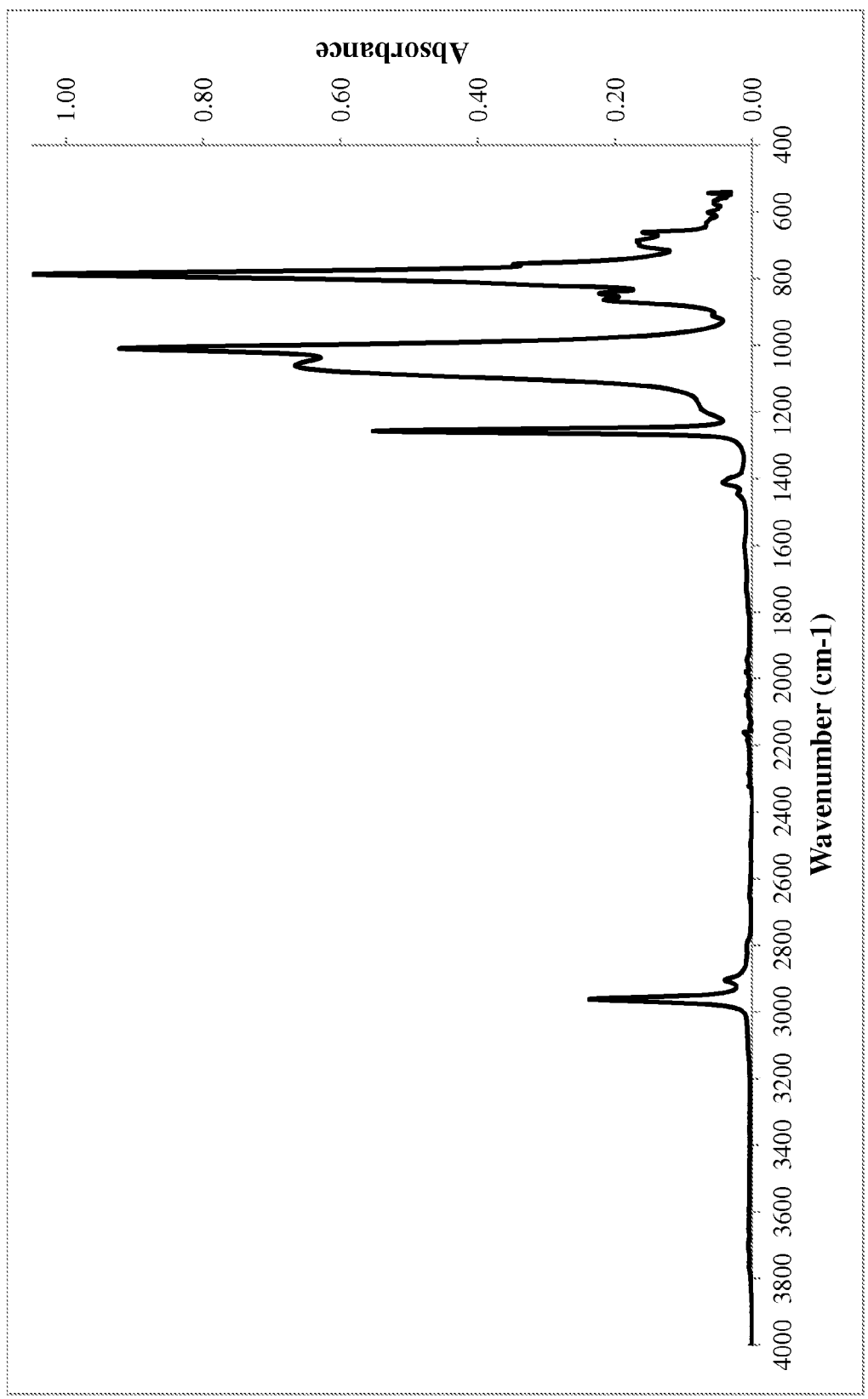
FIG. 11 is the Fourier transform infrared (FTIR) spectrum obtained for the Yellow kit blank. The spectra for the blanks of the other three kits are substantially similar FIG. 12 is a FTIR spectrum of sodium hyaluronate (NaHA) obtained during the experiment.

Commercially available terminating agents containing protected alcohols, amines, and carboxylic acids, employ strongly basic deprotection schemes which depolymerize the polysiloxane chain, or mildly basic deprotection schemes that preserve the siloxane chain but result in direct beta elimination of the functional group itself (these terminating agents are highly reactive and find use in termination of anionic polymerizations of carbon based monomers). As a result, and without wishing to be bound by theory, an efficient introduction of chain end functionality may be achieved through agents with deprotection schemes that are only very mildly basic or, preferably, acidic in nature, and which resist undesirable elimination reactions. Potential solutions are depicted in Schemes 4a and 4b (FIGS. 8 and 9), and involve either a TBDMS-protected organolithium initiator, or synthesis of several suitable terminating agents with mild deprotection protocols compatible with these polysiloxane systems.

In one embodiment, from these functional polysiloxane molecules, introducing controlled free radical polymerization agents such as those for atom-transfer radical-polymerization (ATRP) and reversible addition-fragmentation chain-transfer (RAFT) is straightforward (from 6' and 7' in Scheme 4b of FIG. 9, for example) and can be accomplished in a manner similar for the polydiene analogs. As with the polydiene system, in one embodiment, conversion of the pendant vinyl groups to epoxide groups will be accomplished using mild oxidizing agents such as meta-chloroperbenzoic acid (mCPBA). The timing of this step may depend on the nature of the terminal functional group, and whether it can withstand the oxidative chemistry associated with the epoxidation.

As discussed herein, and without wishing to be bound by theory, PEO (anionic ROP) and poly(N-isopropylacrylamide) (PNIPAM) may be used as secondary blocks based on the potential impact of biocompatible elastomers in the biomedical, microfluidics, and biological microelectromechanical (BioMEMS) areas. As such, epoxidized PVMS-PEO (ePVMS-PEO, via hydrosilylation coupling) and ePVMS-PNIPAM (via RAFT) BCPs are generated for photocuring experiments.

In one embodiment, the morphologies that can be trapped are those expressed by the BCP system in its final, photocurable form, complete with dispersed onium photoacids as proposed in the present disclosure. In one embodiment, understanding the impact of adding epoxide groups to the polydiene and polysiloxane main chains, and the subsequent effects of adding the photoacid generator is a notable aspect of this disclosure.

In one embodiment, phase separation and morphological selection may depend on changes in the net volume fraction occupied by each domain, and the strength of the interaction parameter ($\chi$) governing the enthalpic driving force to phase separate. In one embodiment, both parameters may be affected by the relative amounts of epoxide units and photoacid molecules added to the system. In one embodiment, correlations among epoxide content, photoacid concentration, and phase behavior are established through a combination of small-angle X-ray scattering (SAXS), transmission electromicroscopy (TEM), and rheological measurements.

In one embodiment, the extent to which phase boundaries are shifted and self-assembly is affected is characterized. In one embodiment, photoacid selection (many variants are available) may be a notable factor in achieving adequate distribution to the epoxidized polydiene domain. In one embodiment, a combination of DSC and actual curing experiments may help establish appropriate candidates if solubility issues arise. In one embodiment, primary characterization tools used during this phase may be SAXS, rheology, differential scanning calorimetry (DSC), nuclear magnetic resonance (NMR) spectroscopy, size-exclusion chromatography (SEC), and TEM.

In one embodiment, once the influence of epoxide addition and photoacid concentration on baseline phase behavior (across the phase diagram) is established, their subsequent impact on curing performance may be evaluated. In one embodiment, once UV radiation is introduced, the chemical nature of the system may change as the photoacid degrades and the epoxides open. In one embodiment, the cationic chain polymerization rate may be sufficiently rapid to cross-link the structure before the self-assembled state is influenced by this chemical change in composition. Likewise, in one embodiment, the propagation of the epoxide polymerization may be possible without significant chain reorganization to bring reactive sites and unreacted epoxide groups in contact.

Figure 4:
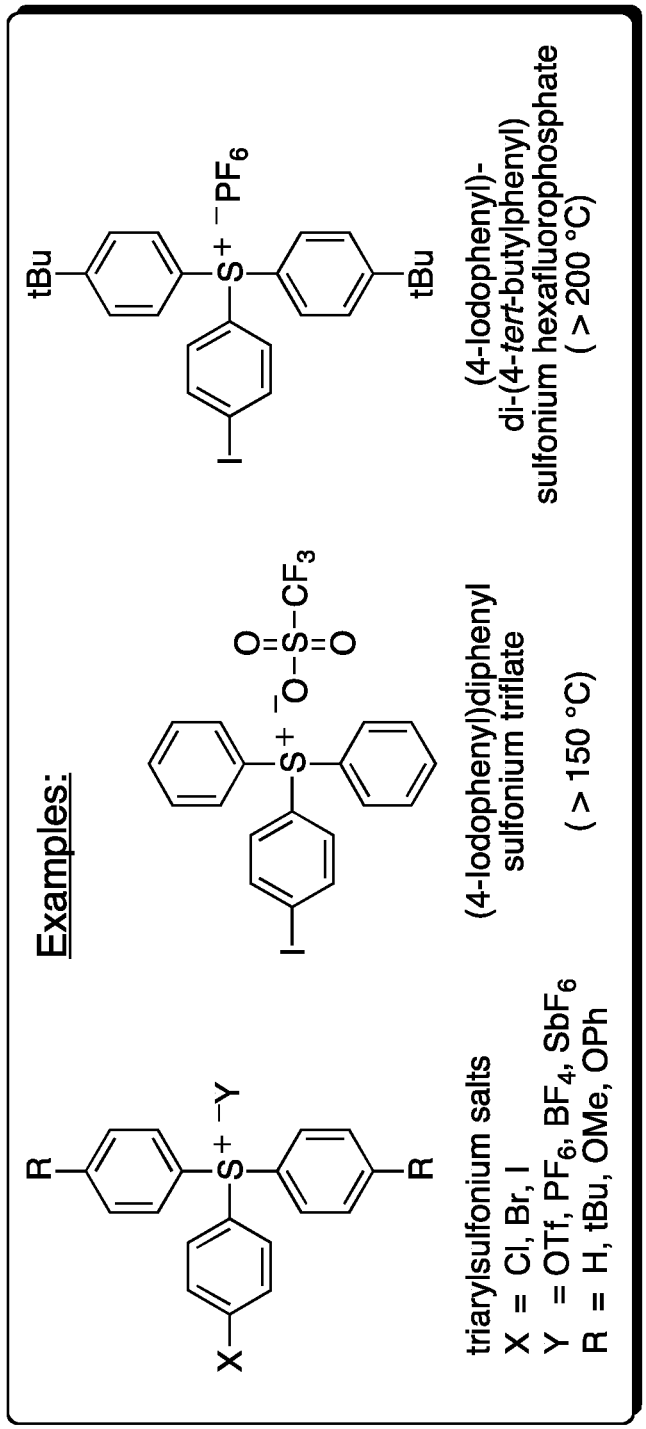
FIG. 4 shows thermally stable photoacids used for curing epoxide-containing polysiloxanes.

In one embodiment, the role of cyclization through intra-chain backbiting as depicted in FIG. 4 affects the efficacy of the trapping process. In one embodiment, the percolation threshold of epoxide units and the related minimum concentration of photoacid are determined and may be morphology dependent. The fidelity of the trapped morphology relative to its degree of organization in the melt prior to cure may be a function of both of these quantities. Similarly, in one embodiment, the intensity of the incident UV light, cure time, and sample thickness, and epoxide conversion may be factors in the fidelity of the trapped morphology.

In one embodiment, the demonstration of the extent to which the system is indeed tolerant of extended thermal processing without the premature initiation of cure may be a major component of this task. In one embodiment, the ability to use temperature to move freely between morphological states and induce cure at will through the radiation trigger is a notable result. Furthermore, in one embodiment, the ability to trap multiple morphologies from a single sample, and to do so within narrow phase boundaries may represent high impact results.

In one embodiment, these quantities may be characterized by a collection of techniques. Characterization of the morphology pre- and post-cure may be performed using SAXS and TEM. Post-cure mechanical properties may be examined using dynamic mechanical analysis (DMA) or other mechanical testing. The indirect measurement of curing kinetics may be performed on, for example, a Texas Instruments ARES rheometer with a fast sampling option enabled integrated with a quartz upper plate and a tunable 200 W Xenon-Mercury light source. Although the extent to which epoxide groups have reacted may be established through FTIR, in one embodiment, more extensive quantification of actual reaction kinetics, epoxide conversion, gel fraction, and evolving crosslinked architecture may use more elaborate pre-processing of the cured materials.

In one embodiment, one way to approach this is to reestablish the solubility of the cured BCPs through selective degradation of the polysiloxane main chains while leaving the polyether linkages established during the cross-linking of the epoxide groups intact. Meanwhile unreacted epoxide groups may remain functionally distinguishable. Unreacted epoxide groups may be converted post-cure by flooding the system with light amines, such as methylamine or dimethylamine.

Figure 6:
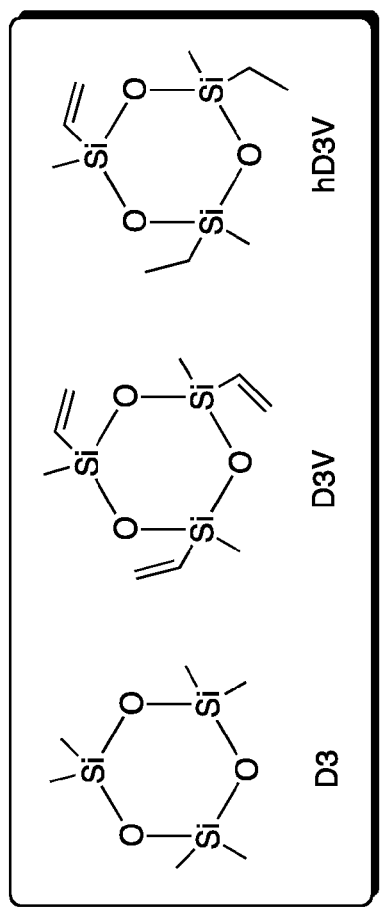
FIG. 6 shows siloxane monomers 1,1,3,3,5,5-hexamethylcyclotrisiloxane (D3) and 1,3,5-trivinyl-1,3,5-trimethylcyclotrisiloxane (D3V) are commercially available. Partial hydrogenation of D3V (hD3V) produces a statistical blend of D3 derivatives containing tunable vinyl content, such as vinyl-1,3,5-trimethyl-3,5-diethylcyclotrisiloxane, as shown.

In one embodiment, polydiene main chains can be degraded through cross metathesis with ethylene or 1-hex-ene, and the polysiloxane main chains degraded using tetra-n-butylammonium fluoride (TBAF) or other base alternatives. For example, FIG. 6 generically represents the degradation products generated from quantitative cross-metathesis of cured polydienes with ethylene gas. Without wishing to be bound by theory, polyether linkages may be inert under both degradation scenarios. In one embodiment, degradation products may be analyzed using combinations of NMR, gas chromatography couple mass spectroscopy (GC-MS), liquid chromatography coupled mass spectroscopy (LC-MS), matrix-assisted laser desorption ionization (MALDI) mass spectroscopy, and size exclusion chromatography (SEC) to quantify not only conversion, but also the chemical and size distribution of polyether products. For example, in one embodiment, the average length of the polyether sequences and the fraction of cyclization products may be analyzed directly.

In one embodiment, the photopatterning capabilities are demonstrating the developed BCP systems introduced in FIG. 2, and their ability to become covalently bound surface modification layers on commercial elastomer resins, such as Sylgard 184™. In some embodiments, the block copolymers disclosed herein may be cast onto devices formed from a silicone-based polymer.

In one embodiment, characterization of pattern transfer, dimensional limitations, and the ability to produce hierarchical patterns may be assessed. In one embodiment, surface characterization methods, such as scanning electron microscopy (SEM) and atomic force microscopy (AFM), may be used.

(c) Guest Molecule

In some embodiments, the guest molecule may be any glycosaminoglycan (GAG). GAGs include any of a group of linear polysaccharides with various disaccharide repeating units and usually occurring in proteoglycans, including chondroitin sulfate, dermatan sulfate, heparan sulfate, and heparin, keratan sulfates, and hyaluronic acid. GAGs may be high molecular weight, low molecular weight, or oligomeric. GAGs or mucopolysaccharides are long unbranched polysaccharides consisting of a repeating disaccharide unit. The repeating unit consists of a hexose (six-carbon sugar) or a hexuronic acid, linked to a hexosamine (six-carbon sugar containing nitrogen). In a particular embodiment, the GAG is a chondroitin sulfate or a hyaluronan, such as hyaluronic acid or derivatives thereof.

In one embodiment, the guest molecule is hyaluronic acid or derivatives thereof. Hyaluronan ("hyaluronic acid," "sodium hyaluronate," or "HA") is a naturally occurring polysaccharide found in tissues and body fluids of vertebrates and in some bacteria. It is a linear polymer with high molecular weight linear polysaccharide containing alternating N-acetyl-D-glucosamine and D-glucuronic acid residues. Derivatives of hyaluronic acid include branched polysaccharides containing alternating N-acetyl-D-glucosamine and D-glucuronic acid residues, and also include the incorporation of further chemical moieties, such as fluorescent labels, glycidyl groups, or protecting groups. Suitable derivatives of hyaluronic acid disclosed herein include, but are not limited to, cetyltrimethylammonium silylhyaluronate (silyl HA-CTA), cetyltrimethylammonium hyaluronate (HA-CTA), hyaluronan salt complex $HA^{2-}QN^+$ (Formula IV), trimethylsilane-protected (TMS-protected)hyaluronan salt complex (Formula V), fluorescein-tagged hyaluronic acid, glycidyl methacrylated hyaluronic acid, and fluorescein-tagged glycidyl methacrylated hyaluronic acid.

HA has relatively high concentrations in the vitreous humor of eye, the umbilical cord, synovial joint fluid, rooster combs, and in native heart valve leaflets, particularly those regions of the valve subject to compression. A carboxyl group (—COOH) is attached to each disaccharide unit of hyaluronic acid. When in solution at physiological pH, hyaluronic acid is ionized, resulting in negatively charged —COO. The negatively charged flexible chains take on an expanded conformation and entangle with each other at very low concentrations, acting as a stiff random coil. In solutions with higher concentration of hyaluronic acid, stiff random coils entangle, forming viscoelastic solutions retaining flow without gelling.

Without wishing to be bound by theory, hyaluronan solutions are viscous at low shear rates, but elastic at high shear rates. Hyaluronic acid's molecular structure leads to its viscoelastic properties, hydrophilicity, and lubricity. Covalently boning HA that is interpenetrated into a polymeric material is more durable than HA surface treatments and coatings. HA is easily produced commercially via fermentation and its availability in high molecular weights results in polymeric materials with large, relatively mobile HA molecules at the surface which should modify hydrophilicity, lubricity, prevent protein adsorption and modified anti-inflammatory properties, and permit efficient, cost-effective commercial scale-up. HA is also available in lower molecular weight and oligomeric forms, which permits tuning to different biological effects than the higher molecular weight species.

Without wishing to be bound by theory, HA is known to bind to three different receptors on endothelial cells (ECs): CD44, hyaluronan-mediated motility receptor (RHAMM), and toll-like receptor 4 (TLR4). CD44 is a cell-surface glycoprotein involved in cell-cell interactions, cell adhesion and migration. RHAMM normally is localized inside the cell and may be involved in transport channels or proteins, flippase activity, and exocytosis. Intracellularly, RHAMM is associated with microtubules and plays a role in the regulation of mitosis. Extracellularly, RHAMM is associated with CD44, and, upon binding to HA, activates intracellular signaling pathways.

Without wishing to be bound by theory, TLR4 plays a fundamental role in pathogen recognition and activation of innate immunity, recognizing pathogen-associated molecular patterns expressed on infectious agents, and mediating the production of cytokines to develop effective immunity. ECs show increased expression of CD44 and TLR4 under inflamed conditions. The interaction of CD44 receptor with HA has been shown to increase vascular endothelial growth factor (VEGF) production and thus promotes cell proliferation. The chain length of HA molecules may significantly affect its interaction with these receptors on ECs. Longer chain HA molecules will most likely have ligands for these receptors which are not as accessible as those on shorter chain HA molecules. HA may also regulate embryonic development, tissue organization, wound healing and angiogenesis.

In one embodiment, salt complexes of hyaluronic acid may be used in forming the polymeric materials. Examples of suitable cations include, but are not limited to, alkyltrimethylammonium chloride, alkylamine hydrochloride, alkylpyridinium chloride, alkyldimethylbenzyl ammonium chloride, alkyltrimethylammonium bromide, alkylamine hydrobromide, alkylpyridinium bromide, and alkyldimethylbenzyl ammonium bromide. Optionally, the HA may be temporarily protected with a protecting group.

In one embodiment, HA may be present in the polymeric material from about 0.001% to about 15% by weight, or 0.2% to about 1.5% by weight.

In some embodiments, the HA concentration is from about 0.2% to about 10% by weight, such as about 5% to about 10% by weight, about 0.5% to about 3.5% by weight, about 0.5% to about 1.0% by weight, about 1.0% to about 1.5% by weight, about 1.5% to about 2.0% by weight, about 2.0% to about 2.5% by weight, about 2.5% to about 3.0% by weight, about 3.0% to about 3.5% by weight, about 3.5% to about 4.0% by weight, about 4.0% to about 4.5% by weight, about 4.5% to about 5.0% by weight, about 5.5% to about 6.0% by weight, about 7.0% to about 7.5% by weight, about 7.5% to about 8.0% by weight, about 8.0% to about 8.5% by weight, about 8.5% to about 9.0% by weight, about 9.0% to about 9.5% by weight, or about 9.5% to about 10.0% by weight.

In other embodiments, the HA concentration in the polymeric material may be about 0.2% by weight, about 0.3% by weight, about 0.4% by weight, about 0.5% by weight, about 0.6% by weight, about 0.7% by weight, about 0.8% by weight, about 0.9% by weight, about 1.1% by weight, about 1.2% by weight, about 1.3% by weight, about 1.4% by weight, about 1.5% by weight, about 1.6% by weight, about 1.7% by weight, about 1.8% by weight, about 1.9% by weight, or about 2.0% by weight.

In one embodiment, the HA may be localized at the surface and in only certain spots if desired, for example to reduce cost, or to modify optical clarity of the ophthalmic device.

In one embodiment, the dry block copolymers may be swollen in aqueous solution with HA, and then the HA may be crosslinked using water-friendly hydroxide or carboxylate chemistry.

In one embodiment, for the hydrogels, a higher HA concentration may be attained than for non-hydrogel, hydrophobic polymer hosts.

(d) Crosslinking Agents

The guest molecules are crosslinked to each other within the polymer host. In one embodiment, to achieve crosslinkage, crosslinking agents are used, such as aliphatic polyisocyanates include, for example, bis(4-isocyanatocyclohexyl) methane ($H_{12}MDI$) such as available from Bayer Corp., Pittsburgh, Pa. under the trade designation Desmodur™ W; isophorone diisocyanate (IPDI) such as commercially available from Huels America, Piscataway, N.J.; hexamethylene diisocyanate (HDI) such as commercially available from Aldrich Chemical Co., Milwaukee, Wis.; trimethylhexamethylene diisocyanate such as commercially available from Degussa, Corp., Dusseldorf, Germany under the trade designation Vestanate™ TMDI; and m-tetramethylxylene diisocyanate (TMXDI) such as commercially available from Aldrich Chemical Co., Milwaukee, Wis. Although typically less preferred, aromatic isocyanates such as diphenylmethane diisocyanate (MDI) such as commercially available from Bayer Corp., Pittsburgh, Pa. under the trade designation Mondur™ M; toluene 2,4-diisocyanate (TDI) such as commercially available from Aldrich Chemical Co., Milwaukee, Wis., and 1,4-phenylene diisocyanate are also useful.

Polyisocyanates include derivatives of the above-listed monomeric isocyanates. These derivatives include, but are not limited to, polyisocyanates containing biuret groups, such as the biuret adduct of hexamethylene diisocyanate (HDI) available from Bayer Corp. under the trade designation Desmodur™ N-100, polyisocyanates based on HDI containing isocyanurate groups, such as that available from Bayer Corp. under trade designation Desmodur™ N-3300, as well as polyisocyanates containing urethane groups, uretdione groups, carbodiimide groups, allophonate groups, and the like. In one embodiment, these derivatives are preferred as they are polymeric, exhibit very low vapor pressures and are substantially free of isocyanate monomer. In one embodiment, other polyisocyanates that may be used are available from Bayer Polymers LLC of Pittsburgh, Pa. under the trade designations Desmodur™ TPLS2294 and Desmodur™ N 3600.

In a particular embodiment, the guest molecule may be crosslinked at the carboxylic acid groups and/or hydroxyl groups using poly(ethylene glycol) diglycidyl ether. Desmodur™ N-3200, a biuret isocyanate derived from hexamethylene diisocyanate, crosslinks hyaluronic acid at the hydroxyl groups, rather than the carboxylic acid groups, preserving hyaluronic acid's lubricity.

In a particular embodiment, the guest molecule may be crosslinked directly to the hydrophilic block of the block copolymer polymer host. In this case, poly(ethylene glycol) diglycidyl ether may be used to facilitate direct crosslinking between the hydroxyl and carboxylic acid groups of the guest molecule and hydroxyl groups of the hydrophilic polymer host, for example polyethylene oxide, polyglycidol, or a random copolymer of polyethylene oxide and polyglycidol.

In one embodiment, different sized guest molecules, such as crosslinked HA molecules, may induce different signaling mechanisms in ECs to promote their adhesion and proliferation.

In one embodiment, the molecular weight ranges for the crosslinked guest molecules may be varied based on crosslinking conditions and the desired biological effect.

In some embodiments, the crosslinked guest molecule may have a large molecular weight, for example from about 10 kDa to about 1 MDa, such as from about 10 kDa to about 50 kDa, from about 50 kDa to about 100 kDa, from about 100 kDa to about 200 kDa, from about 100 kDa to about 200 kDa, from about 100 kDa to about 200 kDa, from about 200 kDa to about 300 kDa, from about 300 kDa to about 400 kDa, from about 400 kDa to about 500 kDa, from about 600 kDa to about 700 kDa, from about 800 kDa to about 900 kDa, or from about 900 kDa to about 1,000 kDa (1 MDa).

In other embodiments, the crosslinked guest molecule may have a molecular weight from about 1 kDa to about 15 kDa, for example from about 1 kDa to about 10 kDa, such as from about 1 kDa to about 2 kDa, from about 2 kDa to about 3 kDa, from about 3 kDa to about 4 kDa, from about 4 kDa to about 5 kDa, from about 5 kDa to about 6 kDa, from about 6 kDa to about 7 kDa, from about 7 kDa to about 8 kDa, from about 8 kDa to about 9 kDa, or from about 9 kDa to about 10 kDa.

In yet other embodiments, the crosslinked guest molecule may be oligomeric, comprising from about 2 to about 15 monomeric units of guest molecules, for example, 6 units or 12 units. In this embodiment, the molecular weight of the oligomeric crosslinked guest molecule is about 0.75 kDa to about 10 kDa, such as for example about 0.75 Da to 1 kDa, from about 1 kDa to about 2 kDa, from about 2 kDa to about 3 kDa, from about 3 kDa to about 4 kDa, from about 4 kDa to about 5 kDa, from about 5 kDa to about 6 kDa, from about 6 kDa to about 7 kDa, from about 7 kDa to about 8 kDa, from about 8 kDa to about 9 kDa, or from about 9 kDa to about 10 kDa.

(e) Method of Making the Polymeric Material

The host polymer may be soaked in a solution of the protected guest molecule. Depending on the nature of the polymer host, the polymer host may swell as it absorbs the solution and the guest molecule diffuses into the host polymer. The polymer host may also wick the soaking solution, such that the solution fills interstitial spaces within the physical structure of the polymer host. The solution may be prepared from a solvent, such as supercritical carbon dioxide, toluene, decalin, trichlorobenzene, or xylenes, and combinations thereof.

In a particular embodiment, the solvent is xylenes.

In one embodiment, viscosity of the soaking solution may be selected to control the rate of diffusion of the guest molecule in to the polymer host.

In a particular embodiment, sodium hyaluronic acid may be complexed with quaternary an ammonium cation, hexadecetyltrimethylammonium bromide, followed by silylation with hexamethyldisilazane to produce silyl HA-CTA. Silylating the hyaluronic acid increases the hydrophobicity of the guest molecule, by replacing the active hydrogens of the hydroxyl groups and amino groups with trimethylsilyl groups. After soaking and crosslinking, the protecting group is removed to free the hydroxyl groups and carboxylic acid groups of the hyaluronic acid. After deprotection, the polymerized guest molecule is hydrophilic.

In one embodiment, the soaking step may occur at a temperature of about 25° C. to about 100° C., for example about 45° C. to about 65° C., such as about 45° C. to about 50° C., about 50° C. to about 55° C., about 55° C. to about 60° C., or about 60° C. to about 65° C.

In one embodiment, the soaking step may occur for about 10 minutes to about 90 minutes, such as about 10 minutes to about 15 minutes, about 15 minutes to about 20 minutes, about 20 minutes to about 25 minutes, about 25 minutes to about 30 minutes, about 30 minutes to about 35 minutes, about 35 minutes to about 40 minutes, about 40 minutes to about 45 minutes, about 45 minutes to about 50 minutes, about 50 minutes to about 55 minutes, about 55 minutes to about 60 minutes, about 60 minutes to about 65 minutes, about 65 minutes to about 70 minutes, about 70 minutes to about 75 minutes, about 75 minutes to about 80 minutes, about 80 minutes to about 85 minutes, or about 85 minutes to about 90 minutes.

In a particular embodiment, the soaking step takes about 60 minutes.

Any concentration below the guest molecule's solubility limit in the selected solvent may be used. In some embodiments, the concentration of guest molecule in the solution may be about 0.5 mg/mL to about 250 mg/mL, for example about 1.5 mg/mL to about 150 mg/mL, or about 2.5 mg/mL to about 50 mg/mL, such as about 2.5 mg/mL to about 5.0 mg/mL, about 5.0 mg/mL to about 10.0 mg/mL, about 10.0 mg/mL to about 15.0 mg/mL, about 15.0 mg/mL to about 20.0 mg/mL, about 20.0 mg/mL to about 25.0 mg/mL, about 25.0 mg/mL to about 30.0 mg/mL, about 30.0 mg/mL to about 35.0 mg/mL, about 35.0 mg/mL to about 40.0 mg/mL, about 40.0 mg/mL to about 45.0 mg/mL, or about 45.0 mg/mL to about 50.0 mg/mL.

After or during formation, the polymer host may be thermally molded in the presence of the protected guest molecule then crosslinking simultaneously. Alternatively, the protected guest molecule may be introduced to the polymer host after curing or molding.

In one embodiment, a diffusion profile of the polymeric material, with its gradual concentration of guest from the outer surface a depth, d, may provide structural integrity of the surface and its associated structure by removing the sharp change in modulus inherent in superficially coating or grafting a surface according to known techniques. In one embodiment, crosslinking to finally produce the polymeric material may be done chemically, thermally, or photochemically.

(f) Surface Modification

The surface may be modified by crosslinking unprotected guest molecule to the guest molecules present at the surface, using any crosslinker described herein. In one embodiment, this additional surface treatment may provide additional well-adhered HA to surface.

In some embodiments, the HA may be directly crosslinked to the block copolymer hydrogels without first modifying them with a guest molecule, such as HA. In other embodiments, UV light may be used to effect crosslinking at the surface of HA modified to be UV curable.

In one embodiment, surfaces may be modified to improve their performance and biocompatibility. Formula (I) represents an unprotected hyaluronic acid.

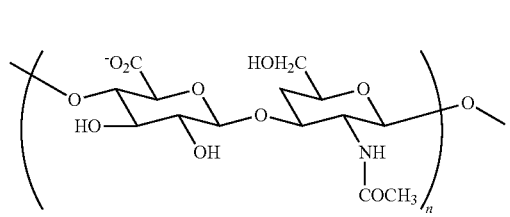

(I)

Possible counterions, generically referred to as "$QN^+$", include, but are not limited to, cetyltrimethylammonium bromide (Formula II) and cetylpyridinium chloride (Formula III). Reaction with the $QN^+$ produces the hyaluronan salt complex $HA^{2-}QN^+$ (Formula IV), which may be protected by reaction with a trimethylsilylation agent, such as chlorotrimethylsilane or hexamethyldisilazane, to yield a trimethylsilane-protected (TMS-protected) hyaluronan salt complex (Formula V). By protecting $HA^{2-}QN^+$ complexes, hydrophilic groups are replaced with silylated functional groups; the hydrogens on the hydroxyl groups and on the amine are replaced with the TMS groups.

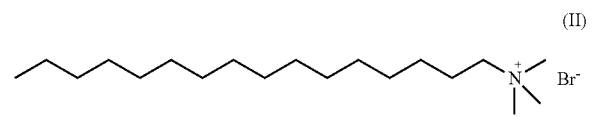

(II)

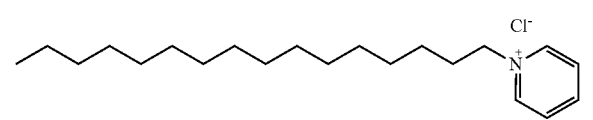

(III)

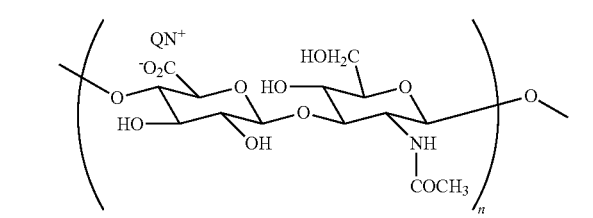

(IV)

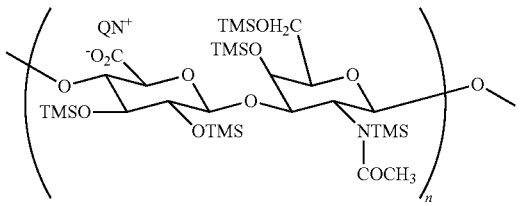

(V)

II. Devices

A polymeric material may be used to manufacture devices used in or contacting the body of a mammal, for example outside or inside a human body. In some embodiments, the polymeric material-containing device contacts the eye. In other embodiments, the polymeric material may be used to produce contact lenses. In yet other embodiments, the polymeric material may be used to produce ocular implants, such as keratoprostheses, corneal inlays and onlays. In other embodiments, the ocular implant may be phakic implant, wherein the native lens of the patient's eye is not removed prior to implantation of the device.

In some aspects, a composite may be used to manufacture devices used in or contacting the body of a mammal, for example outside or inside a human body. In some embodiments, the composite-containing device contacts the eye. In other embodiments, the composite may be used to produce contact lenses. In yet other embodiments, the composite may be used to produce ocular implants, such as keratoprostheses, corneal inlays and onlays.

In one embodiment, the device may be a knee meniscus.

In one embodiment, the devices may be a spinal disk.

(a) Contact Lenses

In one embodiment, the device is a contact lens. The contact lens may comprise a lens body formed from any polymeric material disclosed herein. In one embodiment, the lens body may be washed to remove extractable material from the lens body. In another embodiment, the lens body may be hydrated with an aqueous liquid.

Generally, contact lenses may be classified into soft and hard type lenses. Hard contact lenses are literally hard and can be somewhat uncomfortable to wear. Soft contact lenses are more comfortable to wear, but are commonly removed from the eye at the end of each day. Soft contact lenses may be classified as hydrogel lenses and non-hydrogel lenses.

In one embodiment, the contact lens is a silicone hydrogel contact lens.

In one embodiment, the contact lens can be prepared by lathe-cutting methods, spin casting methods, cast molding methods or combinations thereof, followed by a swelling treatment in a physiological saline and/or phosphate buffered solution. In one embodiment, the contact lens may have a bulk water content of about 20% to about 80% by weight, or about 30% to about 80% by weight. In an alternative embodiment, the contact lens may have a bulk water content of about 1% to about 20% by weight, or about 5% to about 10% by weight. In one embodiment, the contact lens may have a low bulk water content but may have water at the surface.

In one embodiment, the contact lens is ophthalmically compatible. As used herein, the term "ophthalmically compatible" as applied to the contact lenses may also be understood to mean that such lenses and lens bodies are effective to provide the following features in continuous wear applications: (1) allow oxygen to reach the cornea of an eye wearing the lens in an amount sufficient for long-term corneal health; (2) cause no substantial undue corneal swelling or edema in an eye wearing the lens, for example, cause no more than about 10% corneal swelling after being worn on a cornea of an eye during an overnight sleep; (3) allow movement of the lens on the cornea of an eye wearing the lens sufficient to facilitate tear flow between the lens and the eye, in other words, does not cause the lens to adhere to the eye with sufficient force to prevent substantially normal lens movement; (4) allow wearing of the lens on the eye without undue or significant discomfort and/or irritation and/or pain, for example, allow wearing of the lens with substantial comfort and/or substantial freedom from irritation and/or substantial freedom from pain; and (5) inhibit or substantially prevent lipid and/or protein deposition sufficient to substantially interfere with the functioning of the lens during wear, for example, inhibit or substantially prevent lipid and/or protein deposition sufficient to cause the lens wearer to remove the lens because of such deposition. In one embodiment, ophthalmically compatible contact lenses also inhibit, reduce, or even substantially prevent, corneal staining after the lens is continuously worn on a cornea of an eye, for example, during an overnight sleep.

In one embodiment, the contact lens is intended to be worn during the day and removed overnight or to be worn overnight. In one embodiment, the contact lens can be worn continuously for about two weeks. In one embodiment, the contact lens can be worn continuously for about one month or about thirty days. Such continuous wear contact lenses have relatively high oxygen permeabilities to provide for oxygen access to the cornea during the extended wearing of such lenses.

In one embodiment, the contact lens may be comfortable and safe to wear. For example, in one embodiment, silicone hydrogel contact lenses may be comfortable and safe to wear for daily use, for overnight wear, and/or for wearing on an extended or continuous wear basis.

In one embodiment, the lens body has an oxygen permeability, a water content, a surface wettability, a modulus, and a design effective in facilitating ophthalmically compatible wearing of the contact lens by the lens wearer at least for 30 days.

In one embodiment, the lens body has an oxygen permeability, a water content, a surface wettability, a modulus, and a design effective in facilitating ophthalmically compatible wearing of the contact lens by the lens wearer for at least 45 days.

In one embodiment, the lens body has an oxygen permeability, a water content, a surface wettability, a modulus, and a design effective in facilitating ophthalmically compatible wearing of the contact lens by the lens wearer for at least 60 days.

In one embodiment, the lens body has an oxygen permeability, a water content, a surface wettability, a modulus, and a design effective in facilitating ophthalmically compatible wearing of the contact lens by the lens wearer for at least 90 days.

In certain embodiments, the contact lens comprises a soft lens body comprising any polymeric material described herein. In one embodiment, the lens body may have a modulus of less than 1.0 MPa, less than 0.8 MPa, or less than 0.7 MPa. In one embodiment, the lens body may have a modulus in a range of about 0.2 MPa to less than 1.0 MPa.

The oxygen permeability of the contact lenses described herein may be measured with the contact lens in the wet or fully hydrated state. Generally, the oxygen permeability or Dk may be expressed as $10^{-10}$ (ml $O_2$ mm)/(cm$^2$ sec mm Hg) or 1 barrer. In one embodiment, the lens body may have a Dk of at least about 70 barrers, at least about 75 barrers, at least about 80 barrers, at least about 85 barrers, at least about 90 barrers, at least about 95 barrers, at least about 100 barrers, at least about 105 barrers, at least about 110 barrers, at least about 115 barrers, at least about 120 barrers, at least about 125 barrers, at least about 130 barrers, at least about 150 barrers, at least about 180 barrers, at least about 200 barrers, or more.

In one embodiment, lens body may have an oxygen permeability of at least about 50 barrers.

In one embodiment, the lens body may have an oxygen permeability of at least about 120 barrers.

In one embodiment, the lens body may have an oxygen permeability of less than about 200 barrers.

In one embodiment, the relatively high values of Dk of the contact lens may keep the oxygen substantially accessible to the cornea of an eye even when a contact lens is located on the cornea continuously for a prolonged period of time, as described herein.

In one embodiment, to reduce stromal anoxia during daily wear of contact lenses, the lens may have an oxygen transmissibility of at least about 45. In one embodiment, lenses with an oxygen transmissibility greater than 50 may reduce stromal anoxia during daily wear. In one embodiment, to enhance user comfort and wearability, silicone hydrogel contact lenses having reduced modulus, for example, less than 1.0 MPa.

In one embodiment, the surfaces of the contact lens may be modified, if desired, by applying plasma treatment, ozone treatment, corona discharge, chemical reaction and/or other treatment, graft polymerization or the like to increase surface wettability; that is, to increase the wettability of the surface or surfaces of the lens, for example, after molding the lens. In particular embodiments, the surface of the contact lens may be photopatterned with HA as described herein. Such surface treatment, however, is not required.

In one embodiment, the contact lens may be in any suitable configuration effective to satisfy the needs of the lens wearer. For example, in one embodiment, the contact lens may have a single refractive power or two or more refractive powers, such as a bifocal or multifocal lens, or may have no refractive power. In one embodiment, the contact lens can provide spherical corrections, aspherical corrections, cylinder corrections, wave front corrections, corrections of aberrations and the like. Without limitation, examples of useful cylinder correction lenses which may be formed in accordance with the present disclosure are described in U.S. Pat. No. 6,467,903, the disclosure of which is hereby incorporated in its entirety herein by reference.

In one embodiment, the contact lens can be configured to be rotationally stabilized, for example, including ballasts, other rotationally stabilizing features and the like. In one embodiment, the contact lens can be untinted, tinted, colored, for example, with iris-simulating patterns, and the like. In one embodiment, the contact lens can have any suitable edge geometries, such as rounded edges, for example, fully rounded edges from posterior face to anterior face, rounded edges which include portions of the anterior face or the posterior face of the lens and the like. Such rounded edges or edge portions may enhance the comfort and safety of wearing the contact lens, particularly during their extended wear. Without limitation, examples of useful contact lenses with rounded edges which may be formed in accordance with the present disclosure are described in U.S. Pat. No. 6,431,706, the disclosure of which is hereby incorporated in its entirety herein by reference.

The ionoflux of a contact lens or a lens body may be measured, for example, using a technique substantially similar to the so-called "Ionoflux Technique" described in U.S. Pat. No. 5,849,811, the disclosure of which is hereby incorporated in its entirety herein by reference. In one embodiment, the lens body may have an ionoflux of no greater than about $5\times10^{-3}$ mm$^2$/min. In one embodiment, the lens body may have an ionoflux of no greater than about $4\times10^{-3}$ mm$^2$/min, such as no greater than about $3\times10^{-3}$ mm$^2$/min, no greater than about $2\times10^{-3}$ mm$^2$/min, or no greater than about $1\times10^{-3}$ mm$^2$/min.

Overall, the guest molecule within the polymeric material increases the hydrophilicity and lubricity and of the lens body, without substantially changing the oxygen permeability, modulus, and other bulk material properties of the polymer host. Thus, in one embodiment, contact lens wear does not induce dry eye symptoms in patients who have a pre-existing, asymptomatic, marginally dry eye condition. In one embodiment, the polymeric material used in the contact lens increase surface wetting at the corneal epithelium. In one embodiment, wearing contact lens disclosed herein does not thin the preocular tear film and does not interferes with the spreading of mucin onto the cornea.

(b) Ocular Implants

Also provided herein are devices, which are intraocular implants. The intraocular implant may comprise an optic part, comprising a lens formed from any polymeric material disclosed herein. In other embodiments, the intraocular implant may further comprise a haptic part comprising two support loops arranged opposite each other, for supporting the optic part, on both sides of the latter, in anterior chamber of an eye.

In one embodiment, the lens may have a thickness which increases generally from its optical axis toward its periphery, the latter then having an edge of relatively large thickness.

In one embodiment, the lens may be a diverging corrective lens. In one embodiment, the diverging corrective lens may provide a minus optical power. In one embodiment, the diverting corrective lens is a biconcave lens.

In one embodiment, the lens may be a converging corrective lens. In one embodiment, the converging corrective lens may provide a plus optical power.

"Optic" or "optic part" designates in a general manner that part of the implant penetrated by the light rays passing through the pupil, whatever the degree of dilation of the latter. All or part of this optic part can be occupied by the corrective lens itself, of an optical power and geometry appropriate to the desired correction.

"Haptic" or "haptic part" designates that part of the implant which essentially has no role or function with regard to the light rays passing through the pupil, and which ensures in a suitable manner the support, the deployment, and the positioning of the optic part in the anatomical seat of the eye intended to receive it.

In one embodiment, the haptic part and the optic part can be separate. In one embodiment, the haptic part and the optic part can be obtained in monobloc fashion made from one and the same polymeric material.

In one embodiment, the optic part may coincide almost completely with the corrective lens. In one embodiment, the optic part may have a relatively large diameter, such as at least equal to 4.5 mm, to more effectively covering the visual field of the pupil.

In one embodiment, the dimensions and other geometrical parameters of the implant may be generally adapted to the visual condition to be corrected and to the anatomy of the eye receiving the implant.

In one embodiment, the ocular implant, following implantation, reduces the occurrence or diminishes the severity of toxic anterior segment syndrome (TASS), compared to prior art intraocular lenses.

In one embodiment, the ocular implant, following implantation, reduces the occurrence or diminishes the severity of noninfectious endophthalmitis with or without pain, compared to prior art intraocular lenses.

In one embodiment, the ocular implant, following implantation, reduces the occurrence or diminishes the severity of marked decrease in vision, compared to prior art intraocular lenses.

In one embodiment, the ocular implant, following implantation, reduces the occurrence or diminishes the severity of diffuse corneal edema that extends limbus to limbus, compared to prior art intraocular lenses.

In one embodiment, the ocular implant, following implantation, reduces the occurrence or diminishes the severity of photophobia, compared to prior art intraocular lenses.

In one embodiment, the ocular implant, following implantation, reduces the occurrence or diminishes the severity of severe anterior chamber reaction, compared to prior art intraocular lenses.

In one embodiment, the ocular implant, following implantation, reduces the occurrence or diminishes the severity of hypopyon, compared to prior art intraocular lenses.

In one embodiment, the intraocular lens is less inflammatory, eliminates the need for steroidal treatment, and improves or maintains ocular health following implantation, compared to prior art intraocular lenses.

Definitions

As used herein, the terms "about" and "approximately" designate that a value is within a statistically meaningful range. Such a range can be typically within 20%, more typically still within 10%, and even more typically within 5% of a given value or range. The allowable variation encompassed by the terms "about" and "approximately" depends on the particular system under study and can be readily appreciated by one of ordinary skill in the art.

As used herein, the term "w/w" designates the phrase "by weight" and is used to describe the concentration of a particular substance in a mixture or solution.

As used herein, the term "ml/kg" designates milliliters of composition per kilogram of formula weight.

As used herein, the term "monomer" refers to any chemical compound that is capable of forming a covalent bond with itself or a chemically different compound in a repetitive manner. The repetitive bond formation between monomers may lead to a linear, branched, super-branched, or three-dimensional product. Furthermore, monomers may themselves comprise repetitive building blocks, and when polymerized the polymers formed from such monomers are then termed "block polymers". Monomers may belong to various chemical classes of molecules including organic, organometallic or inorganic molecules. The molecular weight of monomers may vary greatly between about 40 Daltons and 20000 Daltons. However, especially when monomers comprise repetitive building blocks, monomers may have even higher molecular weights. Monomers may also include additional reactive groups.

Contemplated polymers may also comprise a wide range of functional or structural moieties, including aromatic systems, and halogenated groups. Furthermore, appropriate polymers may have many configurations, including a homopolymer, and a heteropolymer. Moreover, alternative polymers may have various forms, such as linear, branched, super-branched, or three-dimensional. The molecular weight of contemplated polymers spans a wide range, typically between 400 Daltons and 400,000 Daltons, and may be greater than 1,000,000 Daltons or more, in some embodiments.

"Wettability" refers to the ability of a liquid, such as water, to spread on a solid surface. "Hydrophilic" and "hygrophilic" refer to an intrinsic or average chemical property of a surface or bulk solid to allow a polar liquid, such as water, to spread on the surface, with typical water contact angles from about 0° to about 90°. "Hydrophobic" refers to an intrinsic or average chemical property of a surface or bulk solid that prevents a polar liquid, such as water, from spreading on the surface, with typical water contact angles from about 90° to about 180°, such as from about 100° to about 150°. When the surface roughness enhances or reduces the hydrophilic or hydrophobic properties of a surface or bulk solid, the effect is "parahydrophilic" or "parahydrophobic," respectively. For very rough surfaces, the enhancement or reduction in hydrophilic or hydrophobic properties of the surface or bulk solid may be very great; the effect is referred to as "superhydrophilic" or "superhydrophobic," respectively. Surface roughness is usually defined on the microscopic or molecular scales. For further definition of wettability and surface classifications, please refer to Marmur, "Hydro- hygro- oleo- omni-phobic? Terminology of wettability classification," *Soft Matter,* 8:6867 (2012), which is incorporated herein by reference in its entirety.

The compounds described herein have asymmetric centers. Compounds of the present disclosure containing an asymmetrically substituted atom may be isolated in optically active or racemic form. All chiral, diastereomeric, racemic forms and all geometric isomeric forms of a structure are intended, unless the specific stereochemistry or isomeric form is specifically indicated.

The term "acyl," as used herein alone or as part of another group, denotes the moiety formed by removal of the hydroxy group from the group COOH of an organic carboxylic acid, e.g., RC(O)—, wherein R is $R^1$, $R^1O$—, $R^1R^2N$—, or $R^1S$—, $R^1$ is hydrocarbyl, heterosubstituted hydrocarbyl, or heterocyclo, and $R^2$ is hydrogen, hydrocarbyl, or substituted hydrocarbyl.

The term "acyloxy," as used herein alone or as part of another group, denotes an acyl group as described above bonded through an oxygen linkage (O), e.g., RC(O)O— wherein R is as defined in connection with the term "acyl."

The term "alkyl" as used herein describes groups which are preferably lower alkyl containing from one to eight carbon atoms in the principal chain and up to 20 carbon atoms. They may be straight or branched chain or cyclic and include methyl, ethyl, propyl, isopropyl, butyl, hexyl and the like.

The term "alkenyl" as used herein describes groups which are preferably lower alkenyl containing from two to eight carbon atoms in the principal chain and up to 20 carbon atoms. They may be straight or branched chain or cyclic and include ethenyl, propenyl, isopropenyl, butenyl, isobutenyl, hexenyl, and the like.

The term "alkynyl" as used herein describes groups which are preferably lower alkynyl containing from two to eight carbon atoms in the principal chain and up to 20 carbon atoms. They may be straight or branched chain and include ethynyl, propynyl, butynyl, isobutynyl, hexynyl, and the like.

The term "aromatic" as used herein alone or as part of another group denotes optionally substituted homo- or heterocyclic conjugated planar ring or ring system comprising delocalized electrons. These aromatic groups are preferably monocyclic (e.g., furan or benzene), bicyclic, or tricyclic groups containing from 5 to 14 atoms in the ring portion. The term "aromatic" encompasses "aryl" groups defined below.

The terms "aryl" or "Ar" as used herein alone or as part of another group denote optionally substituted homocyclic aromatic groups, preferably monocyclic or bicyclic groups containing from 6 to 10 carbons in the ring portion, such as phenyl, biphenyl, naphthyl, substituted phenyl, substituted biphenyl, or substituted naphthyl.

The terms "carbocyclo" or "carbocyclic" as used herein alone or as part of another group denote optionally substituted, aromatic or non-aromatic, homocyclic ring or ring system in which all of the atoms in the ring are carbon, with preferably 5 or 6 carbon atoms in each ring. Exemplary substituents include one or more of the following groups: hydrocarbyl, substituted hydrocarbyl, alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxy, keto, ketal, phospho, nitro, and thio.

The terms "halogen" or "halo" as used herein alone or as part of another group refer to chlorine, bromine, fluorine, and iodine.

The term "heteroatom" refers to atoms other than carbon and hydrogen.

The term "heteroaromatic" as used herein alone or as part of another group denotes optionally substituted aromatic groups having at least one heteroatom in at least one ring, and preferably 5 or 6 atoms in each ring. The heteroaromatic group preferably has 1 or 2 oxygen atoms and/or 1 to 4 nitrogen atoms in the ring, and is bonded to the remainder of the molecule through a carbon. Exemplary groups include furyl, benzofuryl, oxazolyl, isoxazolyl, oxadiazolyl, benzoxazolyl, benzoxadiazolyl, pyrrolyl, pyrazolyl, imidazolyl, triazolyl, tetrazolyl, pyridyl, pyrimidyl, pyrazinyl, pyridazinyl, indolyl, isoindolyl, indolizinyl, benzimidazolyl, indazolyl, benzotriazolyl, tetrazolopyridazinyl, carbazolyl, purinyl, quinolinyl, isoquinolinyl, imidazopyridyl, and the like. Exemplary substituents include one or more of the following groups: hydrocarbyl, substituted hydrocarbyl, alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxy, keto, ketal, phospho, nitro, and thio.

The terms "heterocyclo" or "heterocyclic" as used herein alone or as part of another group denote optionally substituted, fully saturated or unsaturated, monocyclic or bicyclic, aromatic or non-aromatic groups having at least one heteroatom in at least one ring, and preferably 5 or 6 atoms in each ring. The heterocyclo group preferably has 1 or 2 oxygen atoms and/or 1 to 4 nitrogen atoms in the ring, and is bonded to the remainder of the molecule through a carbon or heteroatom. Exemplary heterocyclo groups include heteroaromatics as described above. Exemplary substituents include one or more of the following groups: hydrocarbyl, substituted hydrocarbyl, alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxy, keto, ketal, phospho, nitro, and thio.

The terms "hydrocarbon" and "hydrocarbyl" as used herein describe organic compounds or radicals consisting exclusively of the elements carbon and hydrogen. These moieties include alkyl, alkenyl, alkynyl, and aryl moieties.

These moieties also include alkyl, alkenyl, alkynyl, and aryl moieties substituted with other aliphatic or cyclic hydrocarbon groups, such as alkaryl, alkenaryl and alkynaryl. Unless otherwise indicated, these moieties preferably comprise 1 to 20 carbon atoms.

The term "oxygen-protecting group" as used herein denotes a group capable of protecting an oxygen atom (and hence, forming a protected hydroxyl group), wherein the protecting group may be removed, subsequent to the reaction for which protection is employed, without disturbing the remainder of the molecule. Exemplary oxygen protecting groups include ethers (e.g., allyl, triphenylmethyl (trityl or Tr), p-methoxybenzyl (PMB), p-methoxyphenyl (PMP)), acetals (e.g., methoxymethyl (MOM), β-methoxyethoxymethyl (MEM), tetrahydropyranyl (THP), ethoxy ethyl (EE), methylthiomethyl (MTM), 2-methoxy-2-propyl (MOP), 2-trimethylsilylethoxymethyl (SEM)), esters (e.g., benzoate (Bz), allyl carbonate, 2,2,2-trichloroethyl carbonate (Troc), 2-trimethylsilylethyl carbonate), silyl ethers (e.g., trimethylsilyl (TMS), triethylsilyl (TES), triisopropylsilyl (TIPS), triphenylsilyl (TPS), t-butyldimethylsilyl (TBDMS), t-butyldiphenylsilyl (TBDPS) and the like. A variety of oxygen protecting groups and the synthesis thereof may be found in "Protective Groups in Organic Synthesis" by T. W. Greene and P. G. M. Wuts, $3^{rd}$ ed., John Wiley & Sons, 1999.

The "substituted hydrocarbyl" moieties described herein are hydrocarbyl moieties which are substituted with at least one atom other than carbon, including moieties in which a carbon chain atom is substituted with a heteroatom such as nitrogen, oxygen, silicon, phosphorous, boron, or a halogen atom, and moieties in which the carbon chain comprises additional substituents. These substituents include alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxy, keto, ketal, phospho, nitro, and thio.

When introducing elements of the present disclosure or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

Having described the disclosure in detail, it will be apparent that modifications and variations are possible without departing from the scope of the invention defined in the appended claims.

EXAMPLES

The following examples are included to demonstrate certain embodiments of the disclosure. It should be appreciated by those of skill in the art that the techniques disclosed in the examples represent techniques discovered by the inventors to function well in the practice of the disclosure. Those of skill in the art should, however, in light of the present disclosure, appreciate that many changes can be made in the specific embodiments that are disclosed and still obtain a like or similar result without departing from the spirit and scope of the disclosure, therefore all matter set forth is to be interpreted as illustrative and not in a limiting sense.

Example 1: Synthesis of Silyl-HA-CTA

To produce cetyltrimethylammonium silylhyaluronate (silyl HA-CTA), dimethyl sulfoxide (DMSO) was added to cetyltrimethylammonium hyaluronate (HA-CTA) under dry $N_2$ flow. The solution was stirred at 50° C. until the HA-CTA was completely dissolved. The HA-CTA and DMSO solution temperature was increased to 75° C., and hexamethyldisilazane (HMDS) was added under dry $N_2$ flow. The reaction was carried out for at least about 36 hours. Once stirring ceased, the resultant biphasic solution was separated. The top layer was saved and vacuum dried at 50° C. until no change in weight was observed. The bottom layer was discarded. The dry powder, characterized to be silyl HA-CTA, was washed five times with xylenes. The washed silyl HA-CTA was dried again under vacuum at 50° C. vacuum until no change in weight was observed.

Example 2: Protocol for Forming Polymeric Materials (a) Presilylating Glassware

Two pieces of glassware are selected, one to mix the activator and base components and another into which the mixture will be poured and allowed to cure (e.g. a 15 mL beaker for mixing and a petri dish for curing). A small amount of hexamethyldisilazane (HMDS) is poured into glassware, just enough to coat the surface on which the silicone is to cure. HMDS is swirled around such that it contacts the walls of the container. The glassware is allowed to sit overnight in a fume hood to allow HMDS to evaporate.

(b) Curing Normally

Generally, for a normal curing process, activator and base are mixed together in a 1:1 ratio of volumes. The densities are very similar. Using a plastic disposable pipette, base is dispensed into the presilylated "mixing" container. Once the base has been fully loaded into the mixing container, the container refrigerated at 4° C. for 1 hour. Using a syringe without a needle, the desired amount of activator is measured.

Once base has cooled, it is removed from refrigeration and activator is added via syringe evenly over the surface of the base. The components are mixed thoroughly and immediately with spatula for 1 minute, while taking reasonable precaution to avoid introducing bubbles. The mixture is quickly poured into "curing" container. Curing occurs quickly and mixing must be complete within about two minutes of the activator contacting the base.

Optionally, to remove any bubbles been introduced while mixing, the curing container is immediately place under vacuum or agitation in a fume hood and while curing. If not degassed, any bubbles in the curing mixture expand and leave a rice-cake-like disk.

Excess uncured components are washed out using the procedure described below.

(c) Soaking the Polymer Host

An appropriately sized container is chosen, such as a beaker or crystallizing dish. The silicone elastomer swells considerably in xylenes, nearly doubling its dimensions. If the container is not large enough, the elastomer swells out of the container. As a general rule, if any side or dimension of the sample could be doubled without touching both sides of the container's base, then the container is large enough.

Xylenes are poured into the container. The level of xylenes should be about 3 to 4 times the height of the polymer host. The mass of the polymer host is measured before soaking. The polymer host is placed into the xylenes and allowed to swell overnight. The soaked polymer host is then removed from xylenes and excess liquid is patted dry. The mass of the soaked polymer host is recorded. Generally, the polymer host swells to about 2.5 times its previous mass.

The soaked polymer host is placed in vacuum oven to dry at room temperature and −25 inHg (−635 torr). Drying time may depend on sample size, but should generally takes about 2 hours. The solvent may not be entirely removed from the polymer host at this point. The soaked polymer host is placed under vacuum again, this time oven overnight, and the weight was again recorded.

(d) Curing with Xylenes

Adding xylenes prior to curing considerably thins the components, it is easier to mix the activator and base together thoroughly and to cure the polymer host without bubbles, but the curing time is lengthened. The components can be placed into separate vials and mixed with xylenes (4:1 or 1:4 by volume component to xylenes, depending on the level of xylenes desired). Refrigeration is not needed, since the xylenes slow down the curing process. The components can then be poured from the vials into the presilylated mixing container and the procedure from Example 2(b) followed. Since xylenes evaporate during curing, these samples can cure in a fume hood. Any excess uncured components are washed out following the procedure described herein below.

(e) Direct Curing with Silyl-HA-CTA (Via Xylenes)

Direct curing with guest molecule, siliyl-HA-CTA (formed according to Example 1) is performed using the procedures described above in Example 2(b) and (d), with the exception that Silyl-HA-CTA is dissolved into the xylenes at a desired % w/v (percent weight by volume of Silyl-HA-CTA by xylenes). The Silyl-HA-CTA is dissolved into the xylenes before mixing with the components. Any excess uncured components are washed out following the procedure described herein below.

(f) Swelling of the Polymer Host

Day 1: Supply Preparation

Dry silyl HA-CTA guest molecule is placed in a vacuum oven without heat for at least 24 hours. Polymer hosts are weighed and then cleaned by soaking in xylenes for 12 hours in an Erlenmeyer flask with serum stopper or glass coverslip (not parafilm). Any glassware used is dried at least at 100° C. (~125° C.) overnight.

Day 2: Sample Drying, Solution Preparation

Polymer hosts are dried for 12 hours in a vacuum oven with vapor trap without heat.

A silyl HA-CTA solution in xylenes is prepared at the desired concentration, as follows. An Erlenmeyer flask is silylated and a stir bar is rinsed with acetone. The silyl HA-CTA is weighed out. The silyl-HA-CTA is placed in the Erlenmeyer flask with the stir bar. Xylenes are added to the Erlenmeyer flask, for example for a 1.5% w/v HA solution, 100 mL xylenes is added for every 1.5 g silyl HA-CTA. The top of flask is sealed with a serum stopper or glass coverslip. The mixture is stirred at room temperature for about 12 hours until silyl HA-CTA is fully dissolved.

A crosslinking solution of HMDI is prepared in xylenes, as follows. A round-bottomed flask (RBF) is silylated and a stir bar is rinsed with acetone. To the RBF is added 200 ml of 2% (v/v) HMDI in xylenes. The RBF is connected to a condenser and stirred at 50° C. for at least 12 hours.

Day 3: Sample Swelling, Crosslinking, and Acetone Rinse

The weight of the polymer host is recorded and any change in weight is noted. A small crystallizing dish is silylated. The silyl HA-CTA/xylenes solution is place into the dish. The polymer host is allowed to swell in the silyl HA-CTA/xylenes guest molecule solution at ambient temperature for 15 minutes without stirring. The mixture is covered with a glass cover slide. The soaked polymer host is removed and placed in a 50° C. vacuum oven for 3 hours, allowing the solvent to be removed. The weight of the polymer host is recorded and any change in weight is noted.

The crosslinking solution is allowed to cool to ambient temperature and is transferred to a crystallizing dish. The dried and treated polymer host is placed into the dish, and fully submersed for 15 minutes. The mixture is covered with a glass cover slide. The samples are removed and placed in a vacuum oven at 50° C. for 3 hours to crosslink the guest molecule to itself within the polymer host. Polymeric material is removed from vacuum and washed with acetone using the vortexer to remove excess HMDI. The polymeric material is vacuum dried at room temperature until no change in weight is observed in the polymeric material.

(g) Hydrolysis of the Crosslinked Guest Molecule

A hydrolyzing solution of 0.2M sodium chloride in deionized water/ethanol (1:1) is prepared in a large beaker by adding about 5.85 g NaCl to 250 mL deionized water and 250 mL ethanol. The polymeric material is presoaked in xylenes for 5 minutes. The hydrolyzing solution is added to a 500 mL Erlenmeyer flask and sonicated for 60 minutes. The polymeric material is sonicated for 60 minutes in fresh 0.2 M NaCl DI water/ethanol (1:1) hydrolyzing solution. The steps of presoaking and sonicating the polymeric material are repeated at least twice and up to four times.

The polymeric material is presoaked in xylenes for 5 minutes. The polymeric material is swollen in DI water/ethanol (3:2) solution for 2 hours without sonication. The polymeric material is presoaked in xylenes for 5 minutes and then sonicated for 30 minutes in deionized water. The polymeric material is partially dried samples by soaking in acetone for 60 minutes. The acetone is drained and is completely dried in a vacuum oven at 50° C. equipped with a solvent trap at −25 inHg (−635 torr) until weight only changes negligibly. When the polymeric material is dry, the weight is recorded.

Example 3: Preliminary Results for Polymeric Materials

Below are listed some preliminary results illustrating treatment of a polymer host with a solution containing a guest molecule comprising HA:

Plain=Cured normally with no xylenes or silyl-HA silyl-swelled, which means that the polymer host was cured normally without xylenes, but the silyl-HA guest molecule swelled in afterwards.

Silyl-cured=Cured the polymer host with silyl-HA dissolved into xylenes (1:4 component:xylenes). HA content was about 2.5% w/w.

Hyper-xylenes=Cured the polymer host with excess xylenes (1:4 component:xylenes) Hyper-xylenes+silyl-cured=Cured the polymer host with silyl-HA dissolved in excess xylenes (1:4 component:xylenes). The HA content was about 1.9% w/w.

Groups tested: Plain; Plain hydrolyzed; Silyl-swelled hydrolyzed (0.5%); Silyl-swelled hydrolyzed (1.5%); Silyl-swelled hydrolyzed (2.0%); silyl-cured; silyl-cured hydrolyzed; Hyper-xylenes+silyl-cure; Hyper-xylenes+silyl-cure hydrolyzed.

The samples that had silyl-HA cured into them showed significant decreases in mass around 180° C., indicating that roughly 0.5% HA was present in the direct cured polymer materials.

Contact angle goniometry (CAG) indicated an increase in the hydrophilicity of treated samples. The polymeric materials were soaked in phosphate-buffered saline (PBS) solution for several hours to overnight prior to testing. The polymeric materials were kept in PBS until immediately before they were tested, but left out of PBS during testing. The groups tested by CAG were Plain; Plain hydrolyzed; silyl-swelled (0.5%) hydrolyzed; silyl-swelled (1.5%) hydrolyzed; silyl-swelled (2.0%) hydrolyzed; hyper-xylenes cured; hyper-xylenes cured hydrolyzed; silyl-cured; silyl-cured hydrolyzed; hyper-xylenes+silyl cure; hyper xylenes+silyl cure hydrolyzed.

TABLE 1

Contact angle averages

| Sample | 0-min Average (immediately after placing drop) | 1-min average | 3-min average |
|---|---|---|---|
| Plain | 110.81° | 107.92° | — |
| Plain hydrolyzed | 113.17° | 111.13° | — |
| Silyl-swelled (0.5%) hydrolyzed | 113.39° | 111.13° | — |
| Silyl-swelled (1.5%) hydrolyzed | 96.12° | 92.55° | — |
| Silyl-swelled (2.0%) hydrolyzed | 107.67° | 100.63° | 98.50° |
| Hyper xylenes | 103.55° | 95.91° | — |
| Hyper xylenes hydrolyzed | 113.09° | 111.47° | — |
| Silyl-cured | 105.94° | 99.67° | 93.38° |
| Silyl-cured hydrolyzed | 112.30° | 104.70° | — |
| Hyper xylenes + silyl-cure | 109.03° | 103.31° | 102.7° |
| Hyper xylenes + silyl-cure hydrolyzed | 117.74° | 112.98° | — |

Silyl-swelled (1.5%) seemed to show the best improvement in hydrophilicity compared to the Plain sample.

Example 4: Protocols for Characterizing Contact Lenses (a) Optical Transparency

To achieve maximal visual performance, a polymeric material used as a contact lens material should be transparent. The light transmittance properties of polymeric material can be categorized as being transparent, translucent, or opaque. The optical clarity of contact lens polymeric material is expressed as the percentage of transmission of the visible electromagnetic spectrum. Polymeric material lenses should transmit over 90% of light in the visible part of the spectrum to be a good material for contact lens. The optical transparency of contact lens polymeric material was measured using UV/VIS spectrometer.

The transmission measurements were conducted using two different references. In the first experiment, the polymeric material was mounted in the transmission stage and a reference spectrum was captured. In second experiment, the polymeric material was removed from the optical path and a reference spectrum was obtained. The difference between both the spectra was calculated using manufacture provided software to compute % transmission.

(b) Mechanical Properties

The mechanical properties of hydrogel contact lenses formed from a polymeric material disclosed herein are directly related to factors such as comfort, visual performance, fitting characteristics, physiologic impact, durability, and handleability of the lenses. Most hydrogels used for contact lens are soft and flexible when hydrated. When they dehydrate, they become hard and brittle. Unlike elastic materials that deform under stress but return to their original size and shape when stress is released, hydrogels are viscoelastic. They deform time dependently when a stress is applied to them and recover time dependently when the stress is removed.

Exemplary mechanical properties for contact lens are hardness and elasticity. To study the elasticity as well as the adhesive properties of a hydrogel, a glass indenter on an acrylic polymer gel that had been prepared as a thin film on a glass slide was used. The contact area between the indenter and gel layer was computed using fracture mechanics equation, taking into account the thickness of the material, the applied load and radius of the indenter.

(c) Surface Properties

The surface characteristics of a hydrogel contact lens formed from a polymeric material disclosed herein will directly affect its interactions with the tear film and consequently its biocompatibility in the ocular environment. "Wettability" describes the tendency for a liquid to spread on to a solid surface. In vivo, wettability in a contact lens context implies the ability of the tear film to spread and maintain itself over a contact lens surface. The sessile drop and the captive bubble techniques were used to measure the contact angle. Advancing type contact angle may be measured using the sessile drop technique and receding type contact angle may be measured using the captive bubble technique. The receding contact angle obtained is especially important since it may relate to long-term effects of contact lens when it comes in contact with the tear film. The advancing angle corresponds to initial contact of the material with the tear film. Further, the surface roughness interacts with the surface of eye. Atomic force microscope was used to visualize the surface and manufacturer provided software was used to compute the roughness values.

(d) Water Content

The water content of the hydrogel polymeric material was calculated using following formula:

Equilibrium water content (EWC)=(weight of water in polymer/weight of hydrated polymer)×100.

The effect of water content on pH and temperature was also measured. pH ranges from 4 to 9 were investigated. Temperature ranges from 0° C. to 45° C. were investigated.

(e) Oxygen Permeability

Because the cornea receives most of its oxygen from the atmosphere, it is desirable to control the oxygen transmissibility profile of a contact lens formed from a polymeric material disclosed herein. Oxygen permeability is a property of the material itself and is described as the Dk, where D is the diffusivity of the material and k is the solubility of the material. Oxygen permeability of a hydrogel will vary with temperature. The oxygen permeability is also governed by the EWC. The permeability was computed using the following equation:

$Dk = 1.67 \exp(0.0397 EWC)$

To find the amount of oxygen that moves from anterior to the posterior surface, oxygen permeability was divided by the thickness of the length to compute Dk/t. The values of oxygen transport dependent on temperature and pH were also computed.

(f) Refractive Index

A polymeric material fabricated for a contact lens should have a refractive index similar to that of the cornea; that is, near to 1.37. The refractive index was determined by measuring the critical angle of incidence for total internal reflection of light of wavelength 589.3 nm using a calibrated refractometer at different temperatures. Light passes from the prism surface of refractometer into the contact lens material. The critical angle is related by Snell's Law to the refractive index of the specimen tested and of transparent flat reference:

$$n = n' \sin \theta / \sin 90$$

where, n is the refractive index of contact lens material, n' is the refractive index of reference material and θ is critical angle of incidence upon reference surface.

(g) Swell Factor and Dimensional Stability

The dimensional stability of a hydrogel lens refers to its ability to maintain its original dimensions under various conditions. It depends on any factor that changes the water content of the hydrogel or the swelling behavior of the hydrogel. Factors that influence the swell factor of a hydrogel include temperature and pH. The swell factor was computed using following equation:

$$\text{Swell factor (SF)} = \text{Wet dimension/dry dimension.}$$

(h) Protein Adsorption on the Surface of the Polymeric Material

To understand how proteins in tear fluid interact with polymeric material in the contact lens, a solution similar to human tear fluid was prepared containing 1.2 mg/mL lysozyme, 3.88 mg/mL albumin, and 1.6 L mg/ml immunoglobulin G (IgG). The individual protein solutions were prepared in phosphate-buffered saline (PBS). Sterilized polymeric materials were incubated in a 24-wellplate with 500ꞷ solution of individual protein and mixed protein on a horizontal shaker plate (100 rpm) at 37° C. and 5% $CO_2$. After 2 hours of incubation, the protein solution was aspirated followed by three rinses with PBS to remove non-adherent proteins. The protein adsorption was measured using a commercially available micro-BCA assay (Pierce Biotechnology) and the adsorbed protein on surfaces was visualized by SEM imaging.

To measure the protein adsorption using micro-bicinchoninic acid (BCA) assay, the polymeric materials were transferred to a fresh 24-wellplate and incubated with 1% sodium dodecyl sulfate (SDS) solution (Sigma) in PBS on a horizontal shaker plate (100 rpm) for 1 hour. Following incubation, the excess SDS solution with solubilized proteins was collected from each well. The SDS incubation was repeated 2 more times and the resulting SDS solution with solubilized proteins was pooled. The concentration of the total adsorbed protein in the pooled SDS solution was then measured colorimetrically using a micro-BCA assay with a plate reader.

X-ray photoelectron spectrometry (ESCASystems XPS 5800) was used to determine the surface composition of adsorbed proteins on the nanostructured surfaces of the polymeric materials. High-resolution spectra were collected for C1 s peak with a pass energy of 10 eV. Peak fit analysis was performed using Multipack and XPSPeak 4.1 software. Further, the protein adsorbed onto the nanostructured surfaces was air-dried and coated with a 10-nm layer of gold and imaged at 5-7 kV. To detect protein adsorption on the polymeric materials using the mixture solution, the surfaces were stained with antibodies for each protein and imaged using fluorescence microscopy.

(i) Corneal Epithelial Cell Interaction with Hydrogel Materials

Corneal epithelial cell culture medium consisted of Dulbecco-modified Eagle's medium supplemented with 20% human AB serum, 200 mM/mL L-glutamine, 10,000 U/mL penicillin, and 10 mg/mL streptomycin. On the surfaces of the polymeric materials were cultured 10,000 cells/$cm^2$. The cells were grown on polymeric materials for up to 15 days. Cell death was assessed by the Annexin-V-FITC Apoptosis Detection Kit according to manufacturer's recommendations. The proportion of stained Annexin-V+ and Annexin-V+/Propidium iodide+ cells was determined by fluorescence activated cell sorter (FACS) analysis on flow cytometer and data were analyzed using WinMDI freeware.

Microarray analyses were performed using the Affymetrix GeneChip Human Gene 1.0 ST Arrays which contains more than 28,000 gene transcripts. One hundred fifty nanograms of total RNA was subjected to Ambion WT Expression Kit and GeneChip WT Terminal Labeling Kit following the manufacturers' protocols for whole genome gene expression analysis.

Cells grown on the surfaces were fixed in 4% paraformaldehyde for 20 minutes at room temperature. The surfaces were dehydrated and embedded in paraffin after which 3-μm thick longitudinal sections were obtained for staining with hematoxylin and eosin (H&E) according to standard laboratory protocols. Alternatively, immunofluorescent labeling with anti-p63alpha, ABCG2, CK19, CK8/18, Vim and Ki-67 antibodies was used for visualization under a fluorescent microscope.

Example 5: Further Results for Polymeric Materials

The following example provided further experimental details for polymeric materials indicated in the examples above. The polymer hosts studied were commercially available silicone rubbers derived from one of four different two-part silicone kits: XP-565 from Silicones, Inc. ("Red kit"); P-125 from Silicones ("Blue kit"), Inc.; XP-536 from Silicones, Inc. ("Yellow kit"); and LSR 7030 from Momentive ("Green kit") These polymer hosts represent a range of relevant mechanical properties—hardness, density, stiffness, elasticity, component viscosity, and tear resistance—as well as curing requirements, including time and temperature relationships. These kits were chosen for this range of properties to explore any differences that they may have on the degree of success of the treatments. Formation of polymer hosts from these kits is summarized, briefly, as mixing the two components together and allowing the reaction to occur. Heat drastically decreases the time required. The kits are composed of an activator and a base, as above at Example 2.

In this experiment, square slabs (thickness of about 4.5 mm) and thin film (thickness of about 0.23 mm) polymer hosts were used. Each polymer host was formed by combining a two-part resin system thoroughly in a tall container, degassing under vacuum, and pouring the mixture into a container for curing (a culture dish for slabs and on top of an acrylic slab for the films). Bubbles introduced during pouring were also removed. Thin films were spin coated on the acrylic substrate. The mixtures were fully cured under heat as prescribed by the manufacturer for each kit. The polymer host samples were then trimmed to size.

For the square slabs, each kits listed above was used to form a single 6.0 cm round puck. Each puck was then cut to a single 3×3 cm square and further into four 1.5 cm×1.5 cm square samples, resulting 16 square slab polymer hosts (four from each of the four kits).

Similarly, a larger thin film sample was made for each of the above kits and was then cut into smaller sample portions for treatment. Since the resulting thickness of each sample depends strongly on the viscosity of the mixed components, the settings of spin time and speed were investigated for each kit. For the polymer hosts used in this experiment, the average thickness was 0.23 mm. Each kit produced four thin film polymer hosts for a total of 16 thin films among the 4 kits.

Post cure cleaning of the polymer hosts consisted of a series of baths in xylenes, as described above at Example 2. Failure to remove excess components runs the risk of competing molecular influx or efflux at the surface of the polymer host, which may compromise or hinder treatment.

Xylenes can be absorbed into the polymer hosts to produce up to a 180% increase in mass, whereas swelling in acetone produced at most a 20% increase in mass. Moreover, silyl-HA-CTA is more soluble in xylenes than acetone, resulting in better disposition of the guest molecule into the polymer host. On other hand, the HMDI crosslinking agent is more soluble in acetone than xylenes. These two aspects of the solvents presented the possibility of a significant difference in the success of the treatment. Without wishing to be bound by theory, the acetone would only allow the HMDI to penetrate the shallow surface of the polymer host while also minimizing the escape of the silyl-HA-CTA from the polymer host during crosslinking. Thin film polymer hosts could swell to capacity (i.e., equilibrium) in either xylenes or acetone within five minutes, whereas it would take hours the thicker slabs to swell to capacity.

After forming, the polymer hosts were labeled according to their kit and approach designations—i.e. fB1, fB2, fB3, fB4, fR1, fR2, etc—where the preceding "f" denotes that it belongs to the thin film group. The numbered "approach" groups are as follows:

(1) Sham—received all treatments and tests except for silyl-HA-CTA;
(2) Suspended vertically via clip and submerged in the solutions with acetone-HMDI crosslinking solution;
(3) The same as (2) but the a xylenes-based crosslinking solution was used;
(4) Clamped horizontally via metal machine bushings pinched together by binder clips with an acetone-HMDI crosslinking solution.

Except for group (3), all samples had a crosslinking solution with acetone as a solvent. The standard approach 20 minutes in each solution and drying in a heated vacuum oven after each solution. The crosslinking solution was preheated before adding the polymer host and kept at 40° C. during the swelling and that the polymer hosts were dried in a vacuum oven on heat for at least 6 hours.

The variations across the kits:
Green—Polymer hosts in the Green category were treated as stated above without exception.
Blue—Polymer hosts in the Blue category were not dried between the silyl-HA-CTA and HMDI swelling steps. Instead they were dipped in pure xylenes to remove excess solution still clinging on to the surface and then immediately placed in their crosslinking solutions.
Yellow—Polymer hosts in the Yellow category were swelled in both the silyl-HA-CTA and HMDI solutions for 1 hour instead of 20 minutes, except that the approach (3) polymer host was only allowed to swell in its xylenes-HMDI solution for 5 minutes (this change came about from observing how the previous approach (3) polymer hosts had their solution grow opaque after several minutes). In lieu of the 1 hour soak time, fY3 was removed from the solution and left suspended in an empty, covered beaker in the oven (no vacuum).
Red—Polymer hosts were only dried for 25 minutes between swelling stages. Also, all Red group samples were heated in an oven (no vacuum) in empty, covered beakers for 40 minutes immediately after swelling in the crosslinking solution. Similarly, fR3 was only allowed to soak in its crosslinking solution for 5 minutes, but was allowed to heat in the oven for 55 minutes to compensate.

The polymer hosts for the square slab group saw much less variation than the thin film polymer hosts. Each kit had four square slab samples where one was the sham and the other three received identical treatment. This treatment approach is the "sponge swelling" approach described above. In short, a small amount of solution of silyl-HA-CTA and xylenes is dispensed onto the surface of the sample and is allowed to soak in at room temperature. This approach is mimicked with the xylenes-HMDI crosslinking solution. The polymer hosts are covered to prevent evaporation to affect the adsorption. The Yellow group polymer hosts are left uncovered to explore the effect that evaporation would have. The volume of solution dispensed on to each polymer host was found from preliminary "dry-run" tests. The largest volume that could be held on the polymer hosts via the solution's own cohesion forces and was about 0.3 mL of each solution on each sample. The polymer hosts are left to soak up this volume the solution until they appeared to have taken it all up.

The polymer hosts are covered and placed in an oven to be heated while soaking in the crosslinker solution for 1 hour. All samples underwent identical hydrolysis treatments to hydrolyze the silyl-HA-CTA to HA as described above at Example 2.

All samples in both the thin film and square slab groups were tested using a captive bubble contact angle goniometry (CAG). A picture and three quick succession contact angle measurements were taken as soon as the bubble/drop formed on the surface of the polymeric material within 3 seconds of the bubble/drop being released from the dispenser). Another picture and three quick succession contact angle measurements were taken at 45 seconds to determine if the initial measurements were stable. Significant differences between the t=0 and t=45 sec measurements would indicate rearranging on the surface of the polymer materials, which is more of an issue with dry-air contact angle testing. If the polymeric material had any unusual areas or inconsistencies on the surface, steps (1) and (2) were repeated where possible to better characterize the whole surface of the polymeric material.

Within the thin film group, some polymeric materials wrinkled and crosslinked in a permanently wrinkled state—particularly for polymeric materials clamped horizontally. Many of the square slab polymeric materials bowed in such a way that swelling solution pooled at the corners and a large amount of crusty, rough white material resulted in these corners that persisted past acetone washing and hydrolysis. When removed from water for dry-air contact angle testing, these portions also dried, cracked, and peeling off.

Results for the contact angle testing are summarized in Tables 2-5. Where entries in a single slot are separated by a "/" (i.e. x/y) these two number represent contrasting contact angles given by a sample having irregularities on its surface. This is most commonly a glossy area that appears untreated and an opaque (sometimes rough) area that appears heavily treated.

Tables 2 & 3: Average contact angles for each sample tested using captive bubble CAG at the two time points.

| Captive bubble (t = 0) | | | | |
| --- | --- | --- | --- | --- |
| | Blue | Green | Yellow | Red |
| 1 | 105.4 | 144.8 | 113 | 137.4 |
| 2 | — | 158.8 | — | 126.7 |
| 3 | 148.5 | — | — | — |
| 4 | — | — | 135.8 | — |
| 5 | 154 | 128.9 | 139.8 | — |
| 6 | — | — | — | 133.5 |
| 7 | 134.2 | 107.7 | — | 99.3 |

| Captive bubble (t = 45 s) | | | | |
| --- | --- | --- | --- | --- |
| | Blue | Green | Yellow | Red |
| 1 | 105.4 | 143.4 | 98.6 | 135.2 |
| 2 | — | 158.7 | — | 120.4 |
| 3 | 148.5 | — | — | — |
| 4 | — | — | 136 | — |
| 5 | 153.9 | 128.9 | 139.9 | — |
| 6 | — | — | — | 133.6 |
| 7 | 134.1 | 107.7 | — | 99.6 |

Very little change was seen for the majority of samples between t=0 and t=45 s for the captive bubble CAG tests. Any surface reconfiguration due to the presence of water should have already occurred. Some Green kit group polymeric materials seem to have become more hydrophobic according to the Tables 2 & 3.

Tables 4 & 5: Average contact angles for each sample tested using dry-air contact bubble at the two time points.

| Dry-air CAG (t = 0) | | | | |
| --- | --- | --- | --- | --- |
| | Blue | Green | Yellow | Red |
| 1 | 113.6 | 114.4 | 114.2 | 107.3 |
| 2 | 55.1/93.1 | 65.4 | 78.9/85.8 | 103.6 |
| 3 | 60.1 | 104.7 | 89.9 | 104 |
| 4 | 98.7 | 76.8 | 54.5/84.2 | 89 |
| 5 | 70 | — | — | 82.4 |
| 6 | 68.3 | — | — | — |
| 7 | — | — | — | 55.2/67.5 |

| Dry-air CAG (t = 45 s) | | | | |
| --- | --- | --- | --- | --- |
| | Blue | Green | Yellow | Red |
| 1 | 112.7 | 113.9 | 106.4 | 105.6 |
| 2 | 55.2/92.6 | 43.7 | 75.5/81.0 | 94.6 |
| 3 | 55.5 | 102.1 | 85.6 | 97.3 |
| 4 | 91 | 63.1 | 53.8/82.3 | 87.2 |
| 5 | 62.9 | — | — | 76.3 |
| 6 | 61.4 | — | — | — |
| 7 | — | — | — | 50.1/59.9 |

As can be seen above in Tables (4 & 5), some polymeric materials had very different contact angles after 45 seconds elapsed, perhaps indicating that the surface has been treated but reconfigures quickly after drying and rewetting. Many samples showed a notable decrease in contact angle. With the exception of R7, the Red kit group did not do impressively well.

Figure 12:
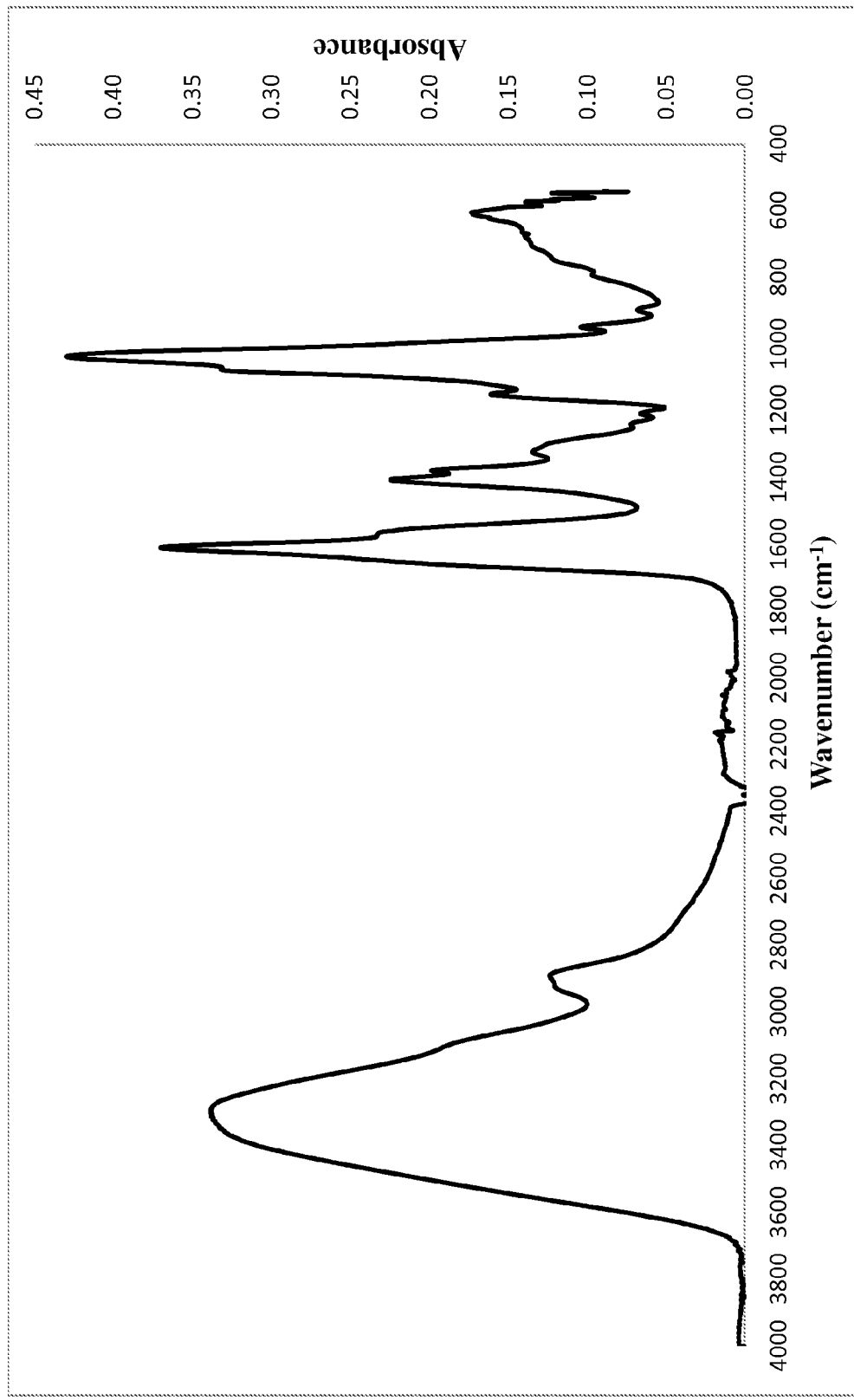
Figure 13:
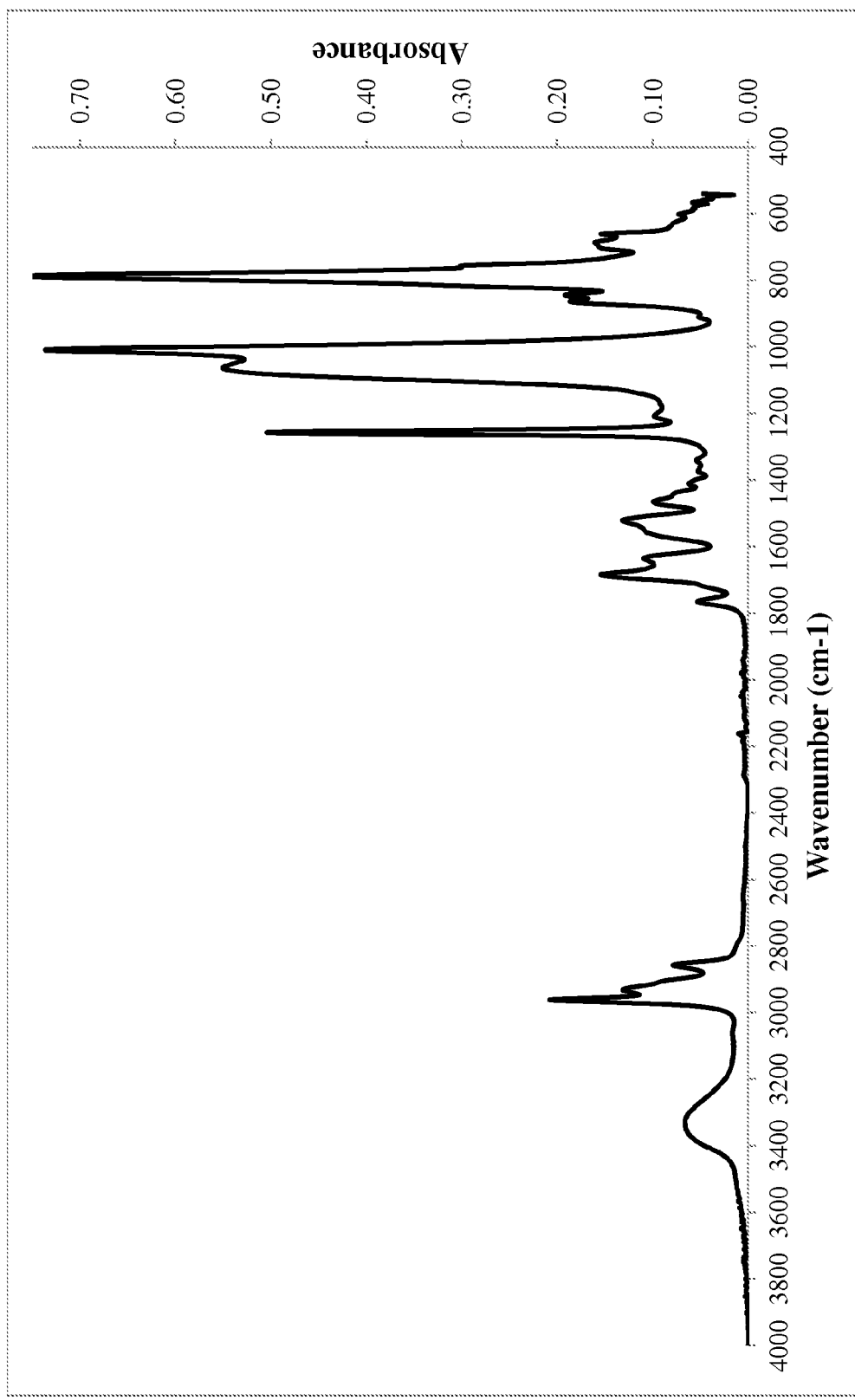
FIG. 13 shows the FTIR spectrum of Red 4 (A).
Figure 14:
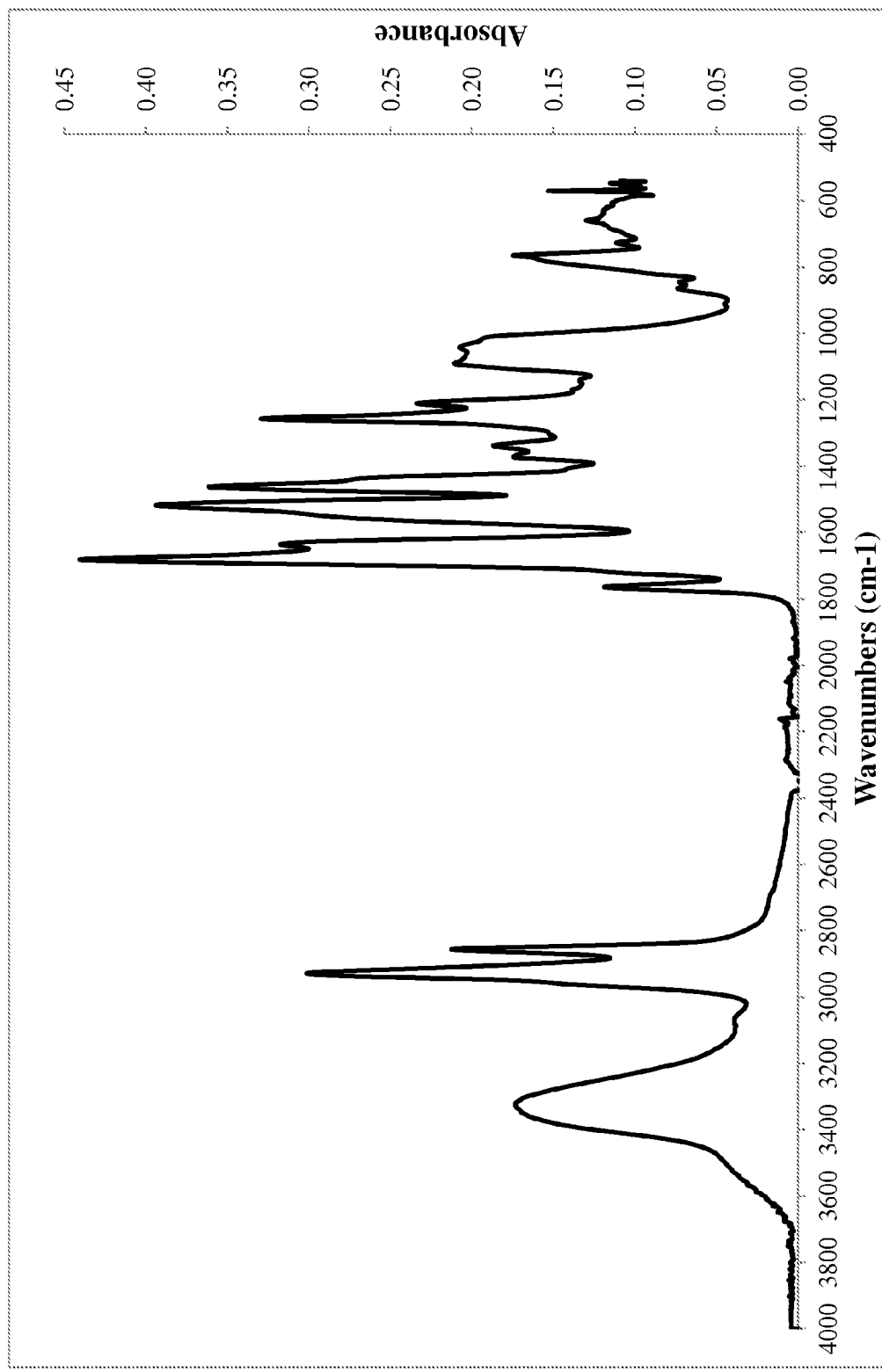
FIG. 14 shows the FTIR spectrum of a so-called "rough spot" on Red 4. Of note, the HA spectrum convolutes the silicone spectrum as surface concentration increases.

Fourier-transform infrared (FTIR) spectroscopy using a Nicolet iS50 FT-IR with an attenuated total reflectance (ATR) attachment was performed on all polymeric materials in the thin film category. FTIR analysis indicated the presence of HA disposed within the polymer hosts. The characteristic peaks for the unmodified polymer hosts agreed with each other among all kits; i.e., the spectra are so much alike between the blanks that they are nearly indistinguishable from each other based on peaks. Along with the spectra for the samples and standards, a spectrum for NaHA (sodium hyaluronate) was taken to aid in the verification of the presence of HA. FIGS. 12, 13, and 14 compare spectra having identifiable HA characteristic peaks and their respective blanks.

The peaks seen in HA below 1320 $cm^{-1}$ occur in the region where several characteristic peaks of silicone are located. The HA characteristic peaks seen in the silicone samples are the broad OH peak at about 3400 $cm^{-1}$, the appearance of a third peak around 2900 $cm^{-1}$, and the series of peaks occurring around 1600 $cm^{-1}$ through 1320 $cm^{-1}$. These ranges of wavenumbers are useful for identifying HA presence due to the low to no activity in those areas for unmodified polymer host. Because the presence of HA in the polymer host begins to distort or engulf the characteristic peaks of silicone, this method does not seem viable for determining HA quantity and will likely remain a qualitative method as there would be no reliable silicone peaks to use as internal standards.

Figure 15B:
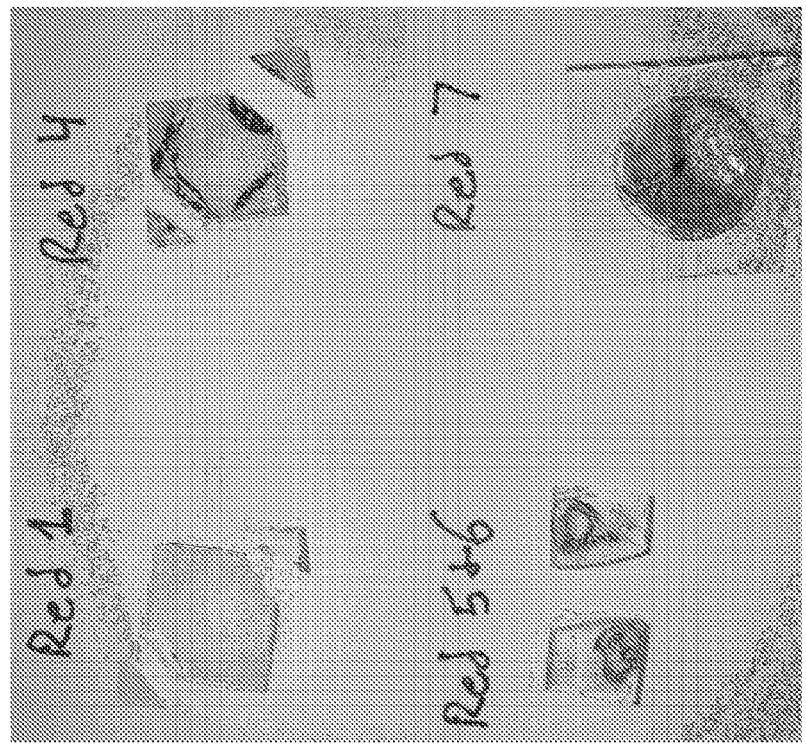
FIG. 15 compares the toluidine Blue O (TBO) results for the Blue (A) and Red (B) kit groups.
Figure 15A:
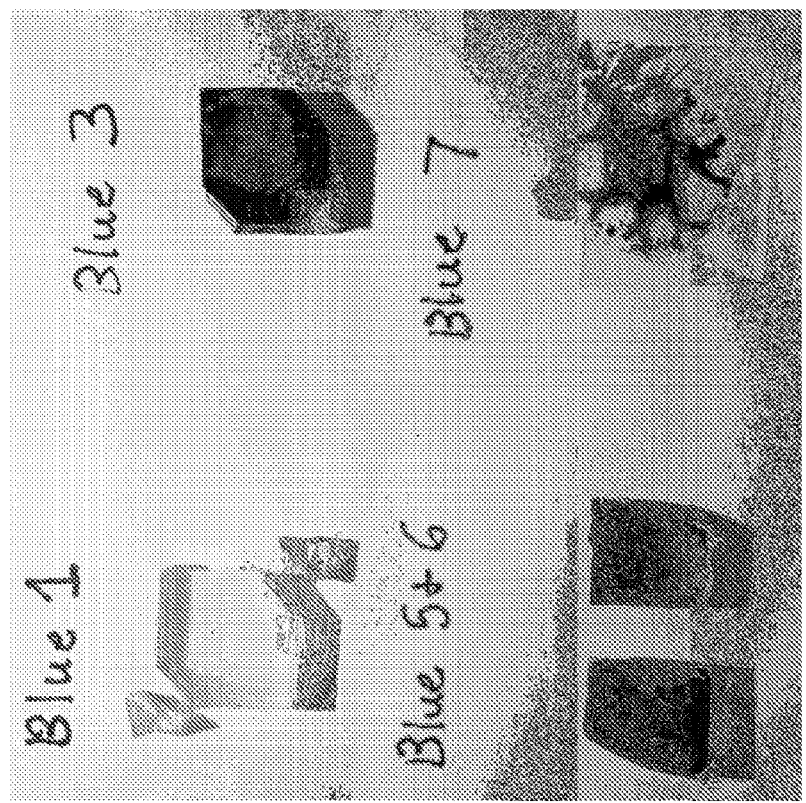

Toluidine Blue O stain was used to detect hyaluronan (HA) on the polymeric materials. The dye stains HA purple, whereas the polymer hosts do not take up any noticeable amount of the aqueous dye. This staining qualitative determines the presence of HA and is limited to the surface, as the polymer host does not allow aqueous staining solution to penetrate deep into the polymeric material. Based on the TBO results, the Blue kit group of samples was treated more successfully than any of the other kit groups. FIG. 15 compares the Blue kit group samples with those of the Red group kit. As can be seen in the same figure below, Red 7 showed a more even and more stable treatment than its counterpart, Blue 7.

Example 6: Photopatterning HA onto Polymeric Materials

Surface photopatterning of hyaluronic acid on the polymeric materials was explored using a polystyrene-poly(ethylene oxide) block (PS-PEO) model. Two dry PS-PEO disks (about 0.1 g) were placed into a 1 mL solution of 0.1 g sodium hyaluronate/mL water and were swollen for 24 hours. Another disk was placed into 1 mL water.

The polymeric materials were designated to 3 groups: (A) No HA (B) HA no XL (C) HA XL. All polymeric materials were subjected to the same reaction conditions; except that group C was subjected to crosslinking through butanediol diglycidyl ether (BDDE). The polymeric material for group C was placed into a solution containing BDDE which is a crosslinker that acts at the primary alcohol on the hyaluronic acid. All polymeric materials were then subjected to a water bath at 40° C. for 8 hours.

Figure 16:
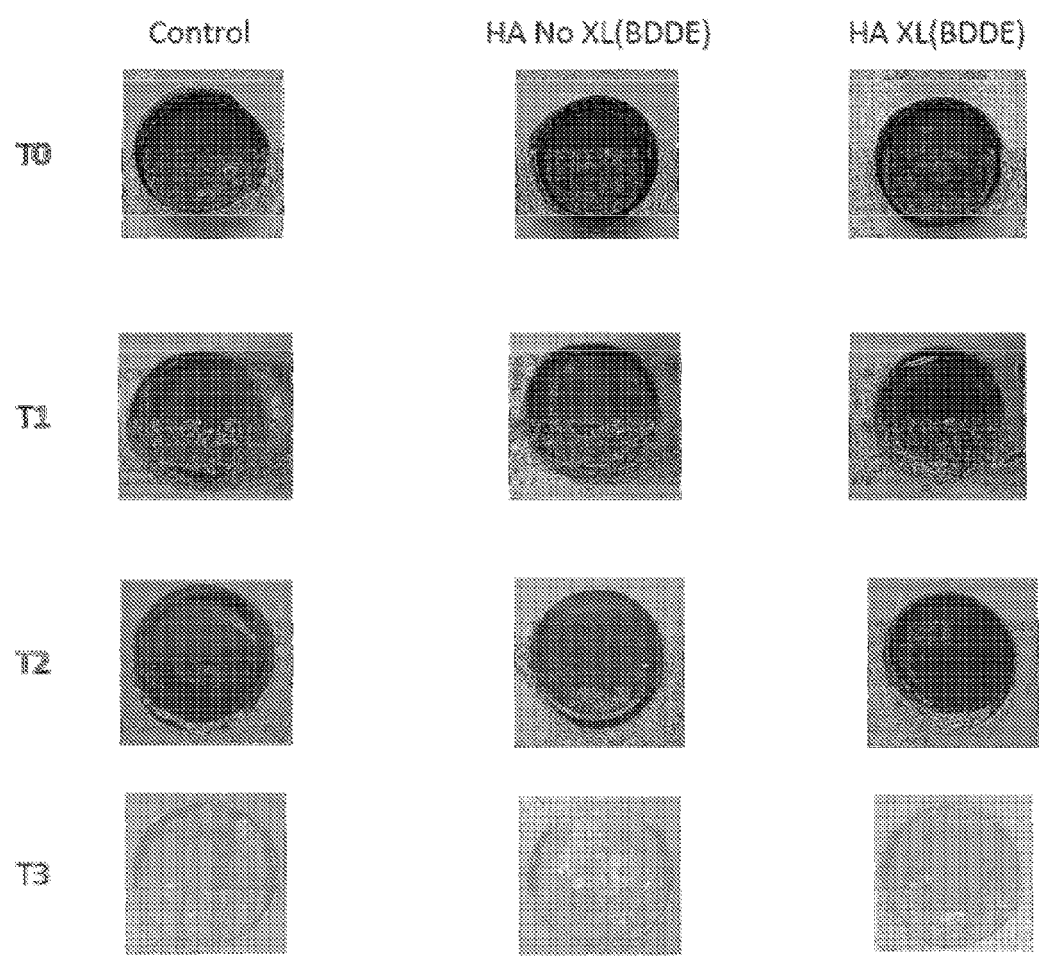
FIG. 16 is a grid of photographs showing TBO-stained polymeric material samples.

Polymeric materials were then placed into a solution containing TBO. They were allowed to soak in this solution for 10 minutes. Upon removal from the solution, the polymeric materials were a dark purple throughout, including the controls. The polymeric materials were then soaked in water for 48 hours, at which point the control showed no color and thus no signs of hyaluronic acid. The gels were monitored for their color periodically throughout this process of leaching of loose TBO, as shown in FIG. 16.

The weakness in using TBO in a hydrogel platform as a label for hyaluronate is that it is a highly entangled polymer network in water and this traps the loose tag for a long period of time (48 hours) making the wait time for the removal of loose dye impractical. Once the control polymeric material showed no loose TBO stain, the polymeric materials were compared, showing clear differences in color. More interestingly the color was more prominent the HA crosslinked through BDDE.

Figure 17:
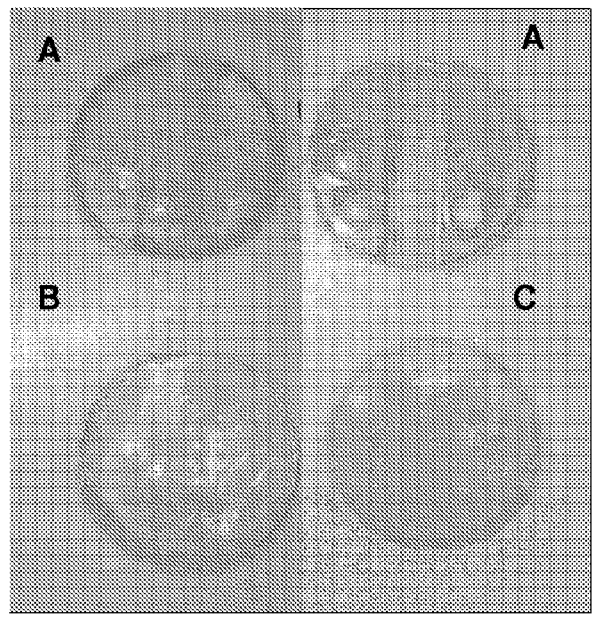
FIG. 17 shows comparison photographs of TBO-stained polymeric material samples.
Figure 18:
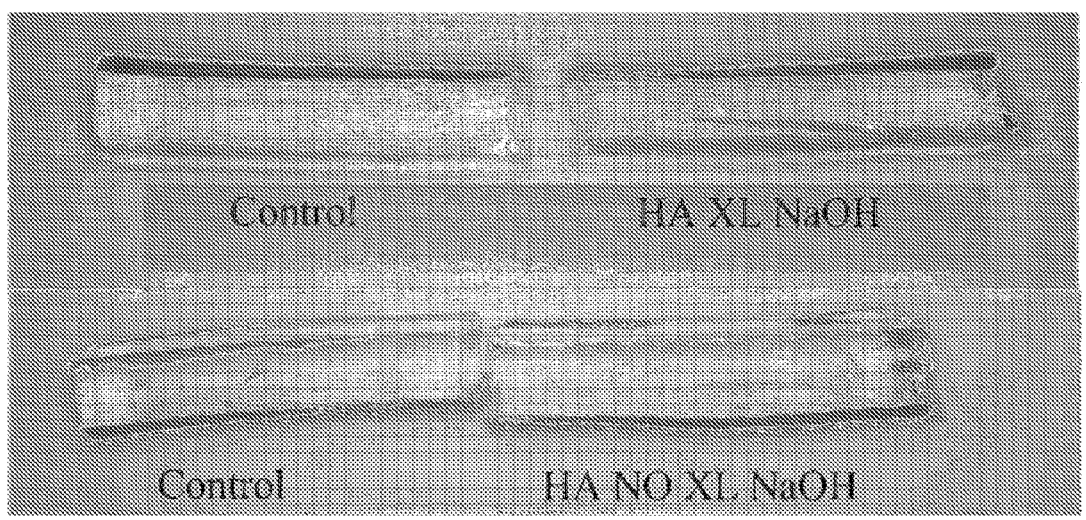
FIG. 18 are photographs of TBO-stained polymeric material samples.

Polymeric materials were cut into three pieces to observe if the HA had penetrated beyond the surface. All polymeric materials revealed no penetration of HA beyond the surface (FIG. 17). The polymeric materials having HA crosslinked by BDDE showed the darkest color and thus the highest hyaluronan content at the surface of the polymeric material.

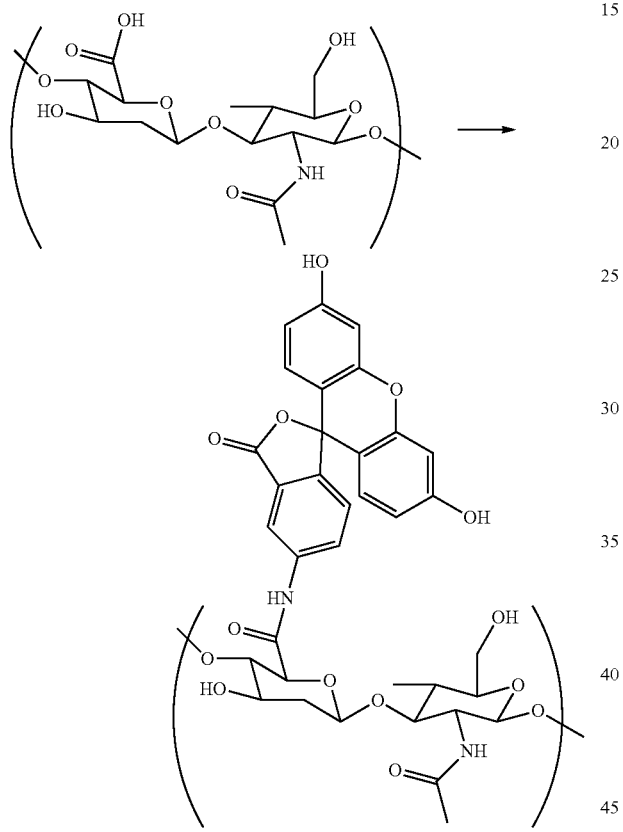

HA was fluorescently labeled with 5-aminofluorescein as depicted in the scheme above. Briefly, 48 mg of HA was dissolved in 12 mL hydrochloric acid/pyridine solution (75/25 wt. %) with a pH 4.75, then 70.5 mg of 5-aminofluorescein and 0.965 g of 1-ethyl-3-(3-dimethylaminopropyl)carbodiimide (EDC) was added. The resulting mixture was allowed to react overnight. Following reaction, the solution was dialyzed against 3.5 L water in dialysis tubing, changing the surrounding water every 12 hours for 48 hours. Once the dialysis was complete and no loose 5-aminofluorescein was visibly present, the solution was precipitated in chilled ethanol with 1.25 wt. % sodium acetate. The precipitate was then centrifuged and dissolved in water and the process was repeated. The pellet recovered from the second centrifugation was dissolved in water and the water was then removed through lyophilization.

Figure 19:
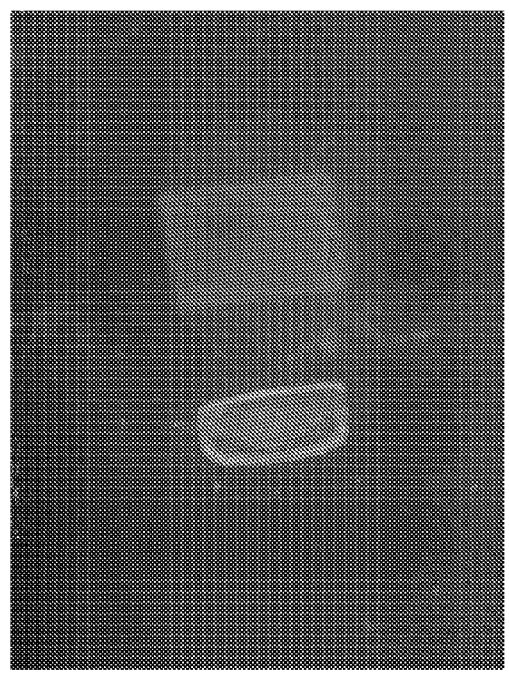
FIG. 19 is a photograph of a control polymer host produced by swelling a dry polystyrene block polyethylene oxide (PS-PEO) polymer host in an hyaluronic acid (HA) solution and examining it under 365-nm filtered ultraviolet (UV) light.

The recovered hyaluronic acid tagged with 5-aminofluorescein was then dissolved in water at a concentration 5 mg per 6 mL water. A dry PS-PEO disk was then swollen in the solution for 24 hours, removed and dabbed to remove any excess solution. A control gel was produced by swelling a dry polymer host disk in an untagged hyaluronic acid solution. The polymer hosts were then examined under a handheld lamp with a 365-nm filter (FIG. 19).

The polymer host that was swollen in the fluorescently tagged HA solution fluoresces indicating a presence of HA in the gel. The gel that was swollen in the untagged HA shows no fluorescent behavior.

A chemical crosslink like that observed in the example shown above with BDDE is one type of crosslinking mechanism for incorporating HA into the hydrogel; another mechanism to generate crosslinks to form an IPN is through photo-crosslinking. This can be done through incorporating a methacrylate group into the HA backbone. This was explored by using glycidyl methacrylate, as depicted in the scheme below. This glycidyl group permits one to pattern the HA on the surface of the polymer host in any desired shape.

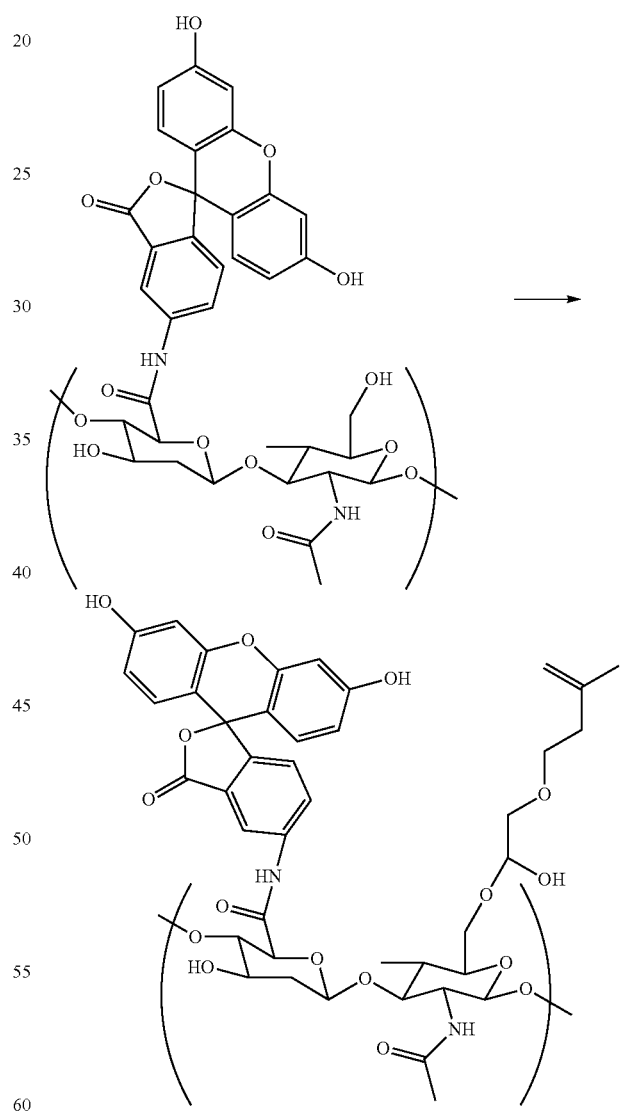

Figure 20A:
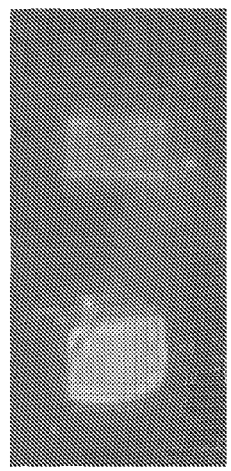
FIGS. 20A, B, and C show polymeric materials treated with fluorescently tagged and examined under 365-nm filtered UV light.
Figure 20B:
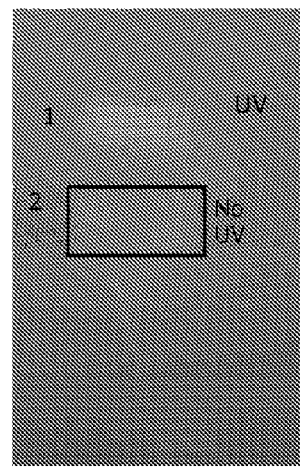
Figure 20C:
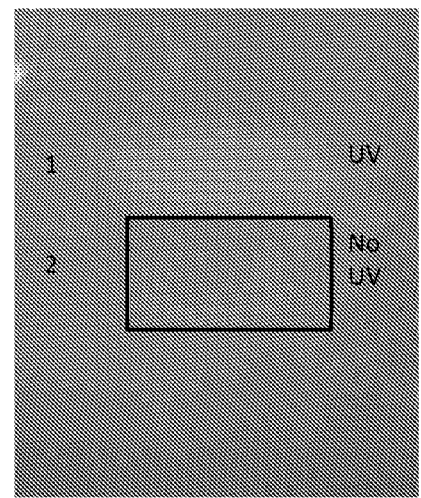
Figure 21A:
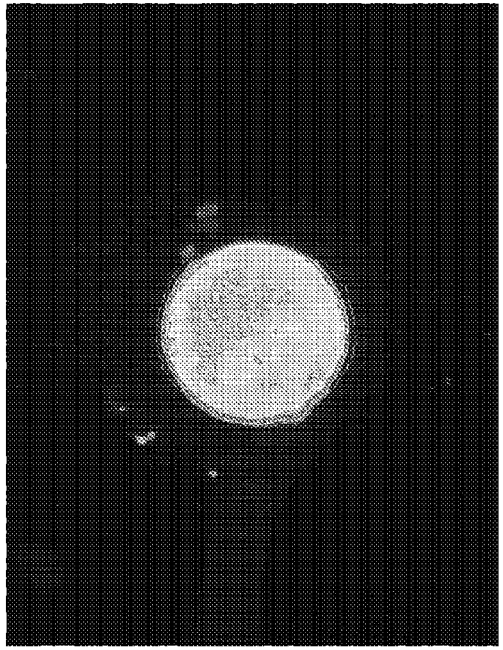
FIGS. 21A and B are photographs indicating photobleaching of fluorescein-tagged HA.
Figure 21B:
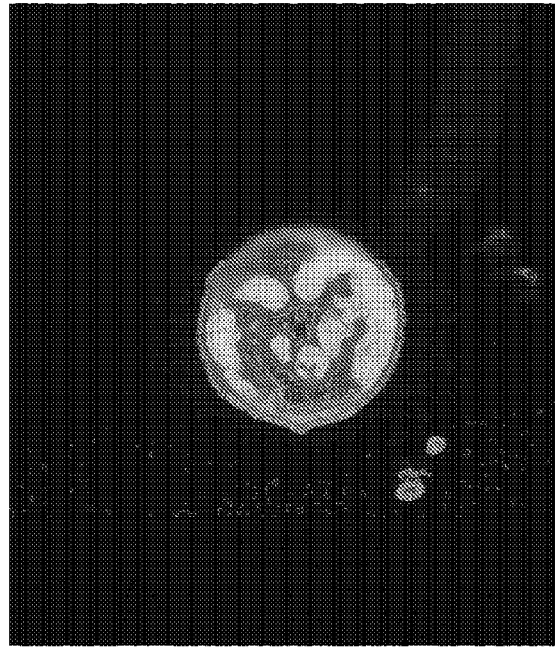

To test if a methacrylate group is necessary for crosslinking of the fluorescently tagged HA, two additional polymeric materials were produced from swelling in a solution of 5 mg fluorescently tagged HA in 6 mL water with 0.5% Irgacure™ 2959 for 24 hours. One of the two polymeric materials was then exposed to 365-nm filtered UV light for 5 minutes. The two gels were then put into 25 mL water and allowed to reach equilibrium for 60 hours. FIG. 20 provides photographs taken under a 365-nm filtered handheld lamp of both polymeric materials, qualitatively revealing through exposure to UV light that the fluorescently tagged HA is trapped in the hydrogel network of the polymer host.

To test if this effect could be amplified, methacrylate-functionalized fluorescent HA was synthesized and used as the guest molecule. The hypothesis being that the additional crosslinking sites of the methacrylate groups has an effect on trapping the HA in the hydrogel network. Briefly, HA was dissolved in a 50/50 wt. % mixture of acetone and water. Twenty molar equivalences of triethylamine and glycidyl methacrylate were added, and the solution was allowed to stir overnight. The methacrylated HA was precipitated into acetone and dissolved in water. This process was repeated and the HA dissolved in water was recovered through lyophilization.

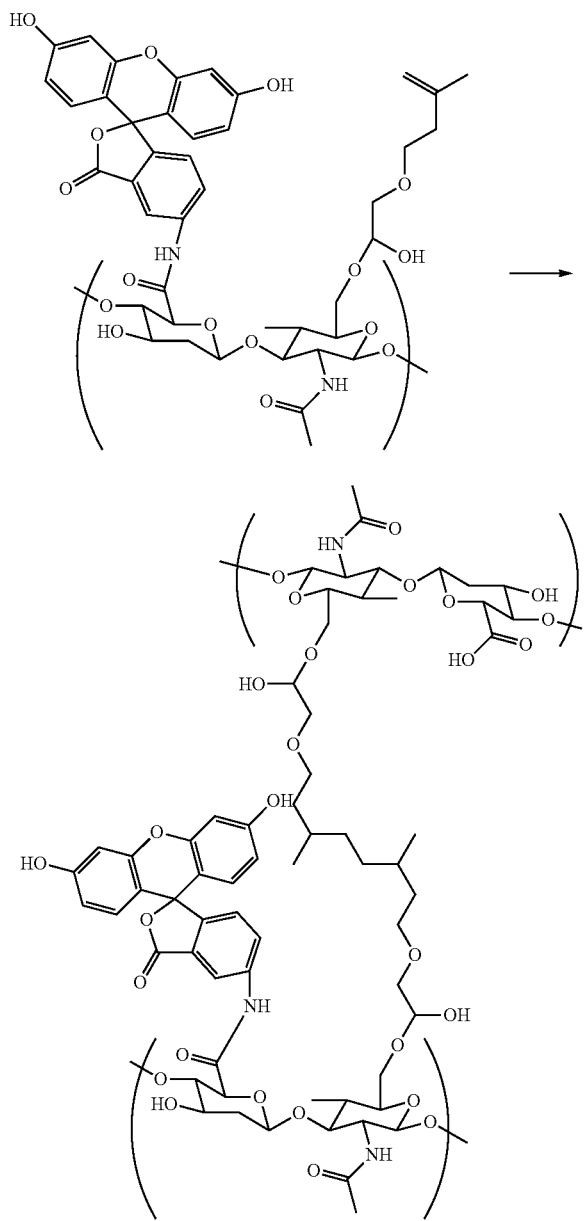

A aqueous solution 1 mg fluorescently tagged methacrylate functionalized HA was prepared. PS-PEO polymer host disks were placed in the solution and allowed to swell and reach equilibrium for 24 hours. Once swollen the gels were placed between two glass microscope slides and a mask, consisting of a transparency with a printed design, was placed on top of the glass microscope slides. The assembly was then placed under 365-nm filtered 22 W/cm$^2$ UV light source for 8 minutes, effecting new covalent bonds to hyaluronic acid from solution, as depicted in the scheme above.

Figure 22A:
FIGS. 22A and B are photographs indicating the cross-linking of HA guest molecule in polymeric materials, without photobleaching the fluorescent label.
Figure 22B:
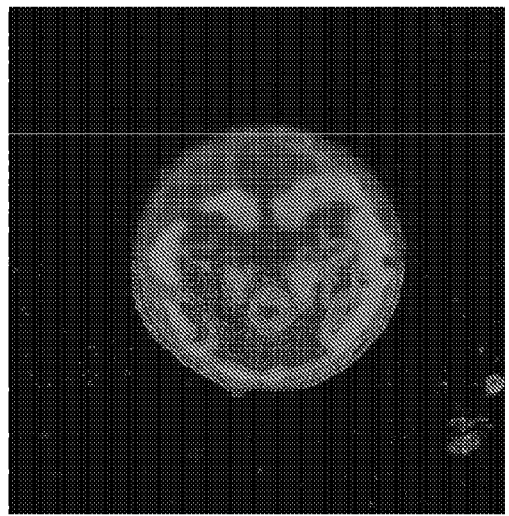

The observed effect was a controlled delivery of UV light. The intensity and exposure time of the light described caused photobleaching of the fluorescein tag of the HA (FIG. 22). Following the exposure to UV light the sample was placed into water and the non-crosslinked HA was allowed to leave the sample. After 60 hours of washing, the pattern was still present on the gel, indicating that the dark portion of the mask let in light at the correct intensity to crosslink but not to photobleach (FIGS. 22A&B)

Figures 23A, 23B, 23C:
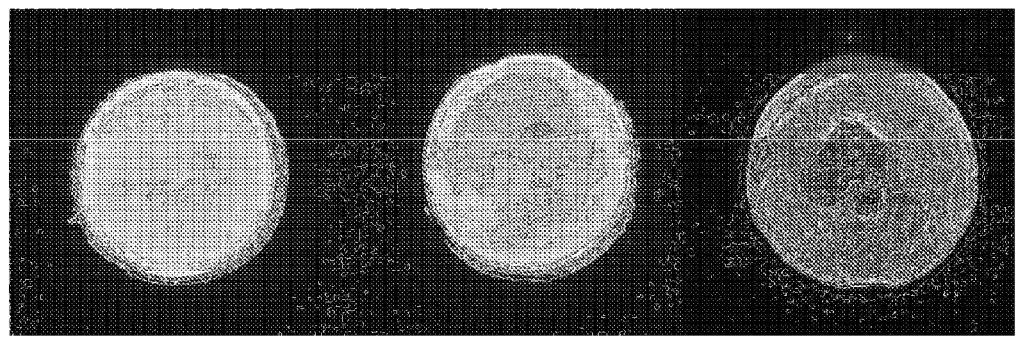
FIGS. 23A, B, and C are photographs indicating the removal of uncrosslinked HA from polymeric materials.
Figures 24A, 24B, 24C, 24D:
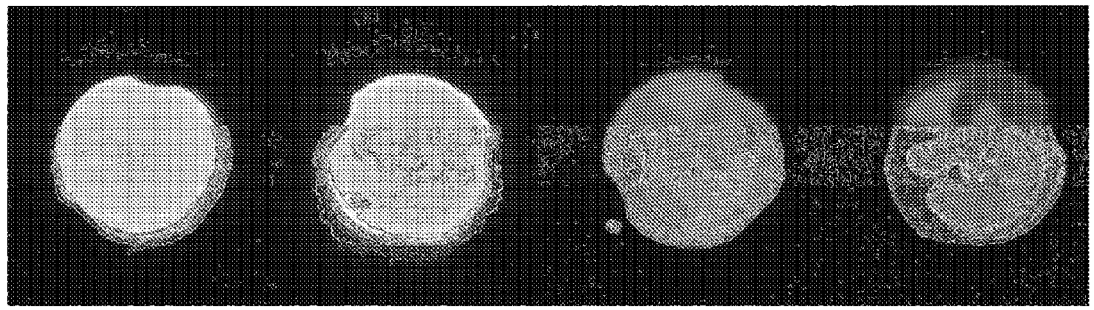
FIGS. 24A, B, C, and D are photographs indicating the effect of an attenuator on samples exposed to UV light.

The experiment was repeated using the same polymeric materials swollen in the same solution using a different. The printed portion of the transparency was used as the portion of the mask that would let the UV light through, where the desired masked region was replaced by a piece of duct tape cut into a square (FIG. 24B). The microscope slide assembly was then placed under 365-nm filtered 22 W/cm$^2$ UV light source for 8 minutes. Following exposure to UV light, the sample was placed into water for 3 hours and the uncrosslinked HA left the hydrogel system of the polymeric material, indicated by the lack of fluorescence in the shape of the duct tape in the center of the gel (FIG. 23C)

Polymeric materials were photopatterned the Colorado State University logo by printing multiple layers of ink over the transparency in the shape of the logo after adding an attenuator to prevent (or substantially reduce) photobleaching. Due to the attenuator, no photobleaching was observed after exposure (FIG. 24B). Following exposure, the sample was placed in water and rinsed for 2 hours (FIG. 24C) and again for 20 hours (FIG. 24D).

What is claimed is:

1. A polymeric material, comprising:
   a polymer host comprising a silicone-based polymer; and
   a guest molecule comprising hyaluronic acid or derivatives thereof;
   wherein the guest molecule is disposed within the polymer host, and
   wherein the guest molecule is covalently bonded to at least one other guest molecule, such that the covalently bonded guest molecules interpenetrate the polymer host molecules.

2. The polymeric material of claim 1, wherein the silicone-based polymer comprises one or more polymers selected from the group consisting of poly(dimethylsiloxane) (PDMS), poly(methylvinylsiloxane) (PVMS), and epoxidized poly(methylvinylsiloxane) (ePVMS).

3. The polymeric material of claim 2, wherein the silicone-based polymer is ePVMS, and the ePVMS has an average molecular weight of 3 kDa to 40 kDa before curing.

4. The polymeric material of claim 1, wherein the silicone-based polymer comprises 3% to 40% vinyl groups per repeated monomeric unit.

5. The polymeric material of claim 1, wherein the contact angle is between 80° and 130°.

6. The polymeric material of claim 1, wherein percentage of covalently bonded guest molecules within the polymer host is 0.2% to 3.5% by weight.

7. The polymeric material of claim 1, wherein average molecular weight of the covalently bonded guest molecule is 0.75 kDa to 10 kDa.

8. The polymeric material of claim 1, wherein the polymeric material resists protein adsorption compared to the polymer host without the guest molecule disposed therein.

9. The polymeric material of claim 1, wherein is light transmission is not substantially diminished compared to the polymer host without the guest molecule disposed therein.

* * * * *